US006964763B1

(12) United States Patent
Crombie et al.

(10) Patent No.: US 6,964,763 B1
(45) Date of Patent: Nov. 15, 2005

(54) METHODS AND COMPOSITIONS FOR INHIBITING HIV INFECTIVITY AND BLOCKING CHEMOKINE ACTIVITY

(75) Inventors: Andrea Rene Crombie, New York, NY (US); Ralph L. Nachman, Englewood Cliffs, NJ (US); Jeffrey C. Laurence, Greenwich, CT (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/555,090

(22) PCT Filed: Nov. 24, 1998

(86) PCT No.: PCT/US98/24905

§ 371 (c)(1), (2), (4) Date: Aug. 7, 2000

(87) PCT Pub. No.: WO99/26649

PCT Pub. Date: Jun. 3, 2000

Related U.S. Application Data

(60) Provisional application No. 60/066,294, filed on Nov. 25, 1997, and provisional application No. 60/078,873, filed on Mar. 20, 1998.

(51) Int. Cl.[7] .................. A61K 38/43

(52) U.S. Cl. .................. 424/94.1; 435/5; 530/350

(58) Field of Search .................. 424/94.1; 435/5; 530/350

(56) References Cited

U.S. PATENT DOCUMENTS

| | | |
|---|---|---|
| 5,426,100 A | 6/1995 | Deutch et al. |
| 5,695,930 A | 12/1997 | Weinstein et al. |
| 5,840,692 A | 11/1998 | Deutch et al. |

FOREIGN PATENT DOCUMENTS

| | | |
|---|---|---|
| EP | 0 807 686 A2 A3 | 11/1997 |
| WO | WO 92/17499 | 10/1992 |
| WO | WO 96/38480 | 12/1996 |

OTHER PUBLICATIONS

Wu, Q. Y., et al., 1991, "Single amino acid substitutions dissociate fibrinogen–clotting and thrombomodulin–binding activities of human thrombin", Proc. Natl. Acad. Sci. USA 88(15):6775–79.*

Peterson, C. B:, et al., 1992, "Long range effects of amino acid substitutions in the catalytic chain of aspartate transcarbamoylase", J. Biol. Chem. 267(4):2443–50.*

Freed, E. O., et al., 1994, "Single amino acid changes in the human immunodeficiency virus type 1 matrix protein block virus particle production", J. Virol. 68(8):5311–5320.*

Valle, R. P., et al., 1998, "Mutagenesis of the NS3 protease of dengue virus type 2", J. Virol. 72(1):624–32.*

Yao, J., et al., 2000, "A single amino–acid substitution of a tyrosine residue in the Rubella virus E1 cytoplasmic domain blocks virus release", J. Virol. 74(7):3029–36.*

(Continued)

*Primary Examiner*—Jeffrey S. Parkin
(74) *Attorney, Agent, or Firm*—Nixon Peabody LLP

(57) ABSTRACT

The present invention relates to a method for suppressing infectivity of HIV which includes contacting the HIV or a cell targeted by HIV with an effective amount of a thrombospondin or a thrombospondin analog. Other aspects of the invention relate to contraceptives, pharmaceutical compositions, and non-contraceptive prophylactic devices that include a carrier and a thrombospondin or a thrombospondin analog. Methods of inhibiting HIV infection in a patient, blocking HIV binding to a cell, blocking chemokine binding to its receptor, and treating or preventing inflammatory states in a patient are also disclosed.

36 Claims, 12 Drawing Sheets

OTHER PUBLICATIONS

Handschuh, G., et al., 2001, "Single amino acid substitutions in conserved extracellular domains of E–cadherin differ in their functional consequences", J. Mol. Biol. 314(3):445–54.*

Back, D. J., 1999, "Pharmacological issues relating to viral resistance", Infect. 27(Suppl. 2):S42–4.*

Yarchoan, R., and S. Broder S. 1992, "Correlations between the in vitro and in vivo activity of anti–HIV agents: implications for future drug development", J. Enzyme Inhibit. 6(1):99–111 (abstract provided).*

Öberg, B. and L. Vrang, 1990, "Screening for new agents", Eur. J. Clin. Microbiol. Infect. Dis. 9(7):466–471.*

Gait, M. J., et al., 1995, "Progress in anti–HIV structure–based drug design", Trends Biotech. 13(10):430–8.*

Crombie, R., et al., 2001, "Peptides derived from salivary thrombospondin–1 replicate its anti–HIV effect: potential role in microbicide development", J. Acquir. Immune Defic. Syndr. 27:91–97.*

Schols, D., et al., 1997, "D RANTES and MCP–3 inhibit the replication of T–cell–tropic human immunodeficiency virus type 1 strains (SF–2, MN, and HE)", J. Virol. 71(10):7300–4 (abstract provided).*

Pichova, I., et al., 1997, "Peptide inhibitors of HIV–1 and HIV–2 proteases: a comparative study", Leukemia 11(S3):120–2 (abstract provided).*

Bellarosa D., et al., 1996, "New arylpyrido–diazepine and –thiodiazepine derivatives are potent and highly selective HIV–1 inhibitors at the reverse transcriptase", Antiviral Res. 30(2–3):109–24 (abstract provided).*

Althaus, I. W., et al., 1993, "Kinetic studies with the non–nucleoside HIV–1 reverse transcriptase inhibitor U–88204E", Biochem. 32(26):6548–54 (abstract provided).*

Crombie et al., "Blockdale of Human Immunodeficiency Virus Infectivity by Salivary Thrombospondin," *Journal of Investigative Medicine Annual Meeting of the Association of American Physicians* 45(3):201A (1997) (abstract).

Crombie et al., "Identification of a CD36–Related Thrombospondin 1–Binding Domain in HIV–1 Envelope Glycoprotein gp120: Relationship to HIV–1–Specific Inhibitory Factors in Human Saliva," *J Exp Med* 187(1):25–35 (1998).

Crombie et al., Lysosomal Integral Membrane Protein II Binds Thrombospondin–1,*Journal of Biological Chemistry* 273(9): 4855–4863 (1998).

Lahav, J., "The Functions of Thrombspondin and its Involvement in Physiology and Pathophysiology," *Biochem Biophys Acta* 1182(1):1–14 (1993).

Tikhonenko et al., "Viral Myc Oncoproteins in Infected Fibroblasts Down–Modulate Thrombospondin–1, a Possible Tumor Suppressor Gene," *The Journal of Biological Chemistry* 271(48):30741–30747 (1996).

Bornstein, P., "Thrombospondins: Structure and Regulation of Expression," *The FASEB Journal* 6:3290–3299 (1992).

Sinnis et al., "Remnant Lipoproteins Inhibit Malaria Sporozoite Invasion of Hepatocytes,"*J Exp Med* 184:945–954 (1996).

Crombie, R., et al., 1997, "Blockade of human immunodeficiency virus infectivity by salivary thrombospondin", J. Invest. Med. (45(3):201A.*

Crombie, R., et al., 1998, "Identificaiton of a CD36–related thrombospondin 1–binding domain in HIV–1 envelope glycoprotein gp120: relationship to HIV–1–specific inhibitory factors in human saliva", J. Exp. Med. 187(1):25–35.*

* cited by examiner

SEQUENCE LISTING

```
<160> NUMBER OF SEQ ID NOS: 14

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  Synthetic
      peptide derived from Homo sapiens thrombospondin-1

<400> SEQUENCE: 1
```

-continued

```
Cys Ser Val Thr Cys Gly
  1               5


<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Val Gly Ser Cys Cys Thr
  1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:  Synthetic
      peptide derived from Homo sapiens thrombospondin-1

<400> SEQUENCE: 3

Gly Arg Gly Asp Ala
  1               5


<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:  Synthetic
      peptide derived from HIV-1 gp120 envelope protein

<400> SEQUENCE: 4

Lys Gln Ser Ser
  1


<210> SEQ ID NO 5
<211> LENGTH: 61
<212> TYPE: PRT
<213> ORGANISM: Homo sapiens

<400> SEQUENCE: 5

Leu Arg Glu Gly Pro Tyr Thr Tyr Arg Val Arg Phe Leu Ala Lys Glu
  1               5                  10                  15

Asn Val Thr Gln Asp Ala Glu Asp Asn Thr Val Ser Phe Leu Gln Pro
             20                  25                  30

Asn Gly Ala Ile Phe Glu Pro Ser Leu Ser Val Gly Thr Glu Ala Asp
         35                  40                  45

Leu Phe Thr Val Leu Asn Leu Ala Val Ala Ala Ala Ala
     50                  55                  60


<210> SEQ ID NO 6
<211> LENGTH: 61
<212> TYPE: PRT
<213> ORGANISM: Homo sapiens

<400> SEQUENCE: 6

Val Lys Gln Gly Pro Tyr Thr Tyr Arg Glu Leu Arg Asn Lys Ala Asn
  1               5                  10                  15

Ile Gln Phe Gly Asp Asn Gly Thr Thr Ile Ser Ala Val Thr Asn Lys
             20                  25                  30
```

-continued

```
Ala Tyr Ile Phe Glu Arg Asn Gln Ser Val Gly Asp Pro Lys Ile Asp
        35                  40                  45

Asn Ile Arg Thr Leu Asn Ile Pro Val Leu Thr Val Ile
    50                  55                  60


<210> SEQ ID NO 7
<211> LENGTH: 16
<212> TYPE: PRT
<213> ORGANISM: Human immunodeficiency virus type 1

<400> SEQUENCE: 7

Gln Phe Thr Asp Asn Ala Lys Thr Ile Ile Val Gln Leu Asn Lys Ser
 1               5                  10                  15


<210> SEQ ID NO 8
<211> LENGTH: 56
<212> TYPE: PRT
<213> ORGANISM: Artificial Sequence
<220> FEATURE:
<223> OTHER INFORMATION: Description of Artificial Sequence:  HIV-1
      clade B consensus

<400> SEQUENCE: 8

Gly Ser Leu Ala Glu Glu Glu Val Val Ile Arg Ser Glu Asn Phe Thr
 1               5                  10                  15

Asn Asn Ala Lys Thr Ile Ile Val Gln Leu Asn Glu Ser Val Glu Ile
            20                  25                  30

Asn Cys Thr Arg Pro Asn Asn Asn Thr Arg Lys Ser Ile His Ile Gly
        35                  40                  45

Pro Gly Arg Ala Phe Tyr Thr Thr
    50                  55


<210> SEQ ID NO 9
<211> LENGTH: 56
<212> TYPE: PRT
<213> ORGANISM: Human immunodeficiency virus type 1

<400> SEQUENCE: 9

Gly Ser Leu Ala Glu Glu Glu Val Val Ile Arg Ser Glu Asn Phe Thr
 1               5                  10                  15

Asp Asn Ala Lys Thr Ile Ile Val His Leu Asn Glu Ser Val Glu Ile
            20                  25                  30

Asn Cys Thr Arg Pro Asn Tyr Asn Lys Arg Lys Ser Ile His Ile Gly
        35                  40                  45

Pro Gly Arg Ala Phe Tyr Thr Lys
    50                  55


<210> SEQ ID NO 10
<211> LENGTH: 57
<212> TYPE: PRT
<213> ORGANISM: Human immunodeficiency virus type 1

<400> SEQUENCE: 10

Gly Ser Leu Ala Glu Glu Glu Val Val Ile Arg Ser Ala Asn Phe Thr
 1               5                  10                  15

Asp Asn Ala Lys Thr Ile Ile Val Gln Leu Asn Glu Ser Val Glu Ile
            20                  25                  30

Asn Cys Thr Arg Pro Asn Asn Asn Thr Arg Lys Ser Ile Arg Gln Arg
        35                  40                  45

Gly Pro Gly Arg Ala Phe Val Thr Ile
    50                  55
```

-continued

<210> SEQ ID NO 11
<211> LENGTH: 18
<212> TYPE: PRT
<213> ORGANISM: Human immunodeficiency virus type 1

<400> SEQUENCE: 11

```
Asn Asn Lys Thr Ile Ile Phe Ser Asn Ser Ser Gly Gly Asp Pro Glu
  1               5                  10                  15

Ile Glu
```

<210> SEQ ID NO 12
<211> LENGTH: 60
<212> TYPE: PRT
<213> ORGANISM: Artificial Sequence
<220> FEATURE:
<223> OTHER INFORMATION: Description of Artificial Sequence: HIV-1 clade B consensus
<220> FEATURE:
<221> NAME/KEY: UNSURE
<222> LOCATION: (22)
<223> OTHER INFORMATION: X at position 22 can be any amino acid

<400> SEQUENCE: 12

```
Ile Arg Gln Ala His Cys Asn Ile Ser Arg Ala Gln Trp Asn Asn Thr
  1               5                  10                  15

Leu Lys Gln Ile Val Xaa Lys Leu Arg Ile Glu Gln Phe Gly Asn Asn
             20                  25                  30

Lys Thr Ile Val Phe Asn Gln Ser Ser Gly Gly Asp Pro Glu Ile Val
         35                  40                  45

Met His Ser Phe Asn Cys Gly Gly Glu Phe Phe Tyr
     50                  55                  60
```

<210> SEQ ID NO 13
<211> LENGTH: 59
<212> TYPE: PRT
<213> ORGANISM: Human immunodeficiency virus type 1

<400> SEQUENCE: 13

```
Ile Arg Gln Ala His Cys Asn Ile Ser Arg Ala Lys Trp Asn Asp Thr
  1               5                  10                  15

Leu Lys Gln Ile Val Ser Lys Leu Lys Ile Glu Gln Phe Lys Asn Lys
             20                  25                  30

Thr Ile Val Phe Asn Gln Ser Ser Gly Gly Asp Pro Glu Ile Val Met
         35                  40                  45

His Ser Phe Asn Cys Gly Gly Glu Phe Phe Tyr
     50                  55
```

<210> SEQ ID NO 14
<211> LENGTH: 60
<212> TYPE: PRT
<213> ORGANISM: Human immunodeficiency virus type 1

<400> SEQUENCE: 14

```
Met Arg Gln Ala His Cys Asn Ile Ser Arg Ala Gln Trp Asn Ala Thr
  1               5                  10                  15

Leu Lys Gln Ile Ala Ser Lys Leu Arg Ile Glu Gln Phe Gly Asn Asn
             20                  25                  30
```

-continued

```
Lys Thr Ile Ile Phe Lys Gln Ser Ser Gly Gly Asp Pro Glu Ile Val
        35                  40                  45

Thr His Ser Phe Asn Cys Gly Gly Glu Phe Phe Tyr
    50                  55                  60
```

METHODS AND COMPOSITIONS FOR INHIBITING HIV INFECTIVITY AND BLOCKING CHEMOKINE ACTIVITY

This application claims benefit of U.S. Provisional Patent Application Ser. No. 60/066,294, filed Nov. 25, 1997, and U.S. Provisional Patent Application Ser. No. 60/078,873, filed Mar. 20, 1998.

This invention was made with support under National Institutes of Health Grant Nos. DE-11348, HL-55646, AI-41327, HL422540, and T32 HL07029. The U.S. Government may have certain rights to this invention.

FIELD OF THE INVENTION

The present invention relates to methods which inhibit HIV infectivity, block HIV binding to a cell, block chemokine binding to its receptor, and treat or prevent inflammatory states in a patient, as well as pharmaceutical compositions, contraceptives, and non-contraceptive prophylactic devices.

BACKGROUND OF THE INVENTION

Acquired immunodeficiency syndrome ("AIDS") has been described as the first great pandemic of the second half of the twentieth century. Gallo, *Sci. Am.,* 256:39 (1987). Human immunodeficiency virus ("HIV") is the etiological agent of AIDS. A complete sequencing of the HIV genome indicates that it contains the same overall gag-pol-env organization as other retroviruses. Ratner et al., "Complete Nucleotide Sequence of the AIDS virus, HTLV-III," *Nature* 313:277–84 (1985). HIV invades a host cell and uses the host cell's machinery to replicate itself.

HIV can be cultured from most tissues and body fluids of infected individuals. Saliva represents a significant exception. In an early report, HIV-1 was isolated from only one of 71 saliva samples of HIV+donors (Ho et al., "Infrequency of Isolation of HTLV-III Virus from Saliva in AIDS," *New Engl. J. Med.* 313:1606 (1985)). Recent work confirmed the paucity of infectious virus in saliva (Groopman et al., "HTLV-III in Saliva of People with AIDS-Related Complex and Healthy Homosexual Men at Risk for AIDS," *Science,* 226:447–449 (1994)), with a mean viral load in 25 samples of 162 genome equivalent/ml, at the limits of detection by reverse transcription-polymerase chain reaction ("RT-PCR") (Liuzzi et al., "Analysis of HIV-1 Load in Blood, Semen and Saliva: Evidence for Different Viral Compartments in a Cross-Sectional and Longitudinal Study," *AIDS,* 10:F10–F56 (1996)). Clinical support for the limited transmissibility of HIV by saliva includes: lack of infection following contamination of open wounds with saliva from HIV+individuals (CDC, "Update: Universal Precautions for Prevention of Transmission of Human Immunodeficiency Virus, Hepatitis B Virus, and Other Blood-Borne Pathogens in Healthcare Settings," *Morbid. Mortal. Wkly. Rep.,* 37:377–388 (1988)); low occupational risk for HIV infection among dentists in practices with large numbers of patients at risk for HIV infection (Klein et al., "Low Occupational Risk of Human Immunodeficiency Virus Infection Among Dental Professionals," *New Engl. J. Med.,* 318:86–90 (1988)); and the inability to infect adult chimpanzees by direct application of HIV to intact oral mucosa (Fultz, "Components of Saliva Inactivate Human Immunodeficiency Virus," *Lancet*, ii: 1215 (1986)).

Such retarded transmission is not a general characteristic of viruses which can be shed orally. The annual attack rate for hepatitis B virus among unvaccinated dentists is 2.6% (Remis et al., "Hepatitis B Infection in a Day School for Mentally Retarded Students: Transmission from Students to Staff," *Am. J. Public Health,* 77:1183–1186 (1987)), human T cell lymphotrophic virus type I is found in saliva (Achiron et al., "Detection of Proviralpuman T-Cell Lymphotropic Virus Type I DNA in Mouthwash Samples of HAM/TSP Patients and HTLV-I Carriers," *Arch. Virol.,* 141:147–153 (1996)), and the type D retrovirus etiologic in a simian immune-deficiency syndrome can be readily isolated from macaque saliva and spread by this fluid (Lercke et al., "Inapparent Carrier of Simian Acquired Immune Deficiency Type D Retrovirus and Disease Transmission with Saliva," *J. Natl. Cancer Inst.,* 77:489–495 (1986)). The ability of saliva to suppress HIV-1 also is relatively specific. It does not alter the infectivity of Herpes simplex virus (Malamud et al., "Human Submandibular Saliva Aggregates HIV," *AIDS Res. Hum. Retroviruses,* 9:633–637 (1993)), and both cytomegalovirus and Epstein-Barr virus are readily shed in oral secretions of HIV seronegative (Fox et al., "Saliva Inhibits HIV-1 Infectivity," *J. Am. Dent. Assoc.,* 116:635–637 (1988)) and seropositive persons (Alsip et al., "Increased Epstein-Barr Virus DNA in Oropharygeal Secretions from Patients with AIDS, AIDS-Related Complex, or Asymptomatic Human Immunodeficiency Virus Infections," *J. Infect. Dis.,* 157:1072–1076 (1988); Scholes et al., "Oral Shedding of CMV and HSV in Relation to HIV Disease," *IXth Intl. Conf. AIDS*, Berlin, June 6 –11:Abst. PO-B18-1801-(1993)).

In contrast, other body fluids from HIV+individuals contain HIV in relatively high titers, including tears (CDC, "Recommendations for Preventing Possible Transmission of Human T-Lymphotropic Virus Type III/Lymphadenopathy-Associated Virus from Tears," *Morbid. Mortal. Wkly. Rep.,* 34:533–534 (1986)), genital secretions (Mostad et al., "Shedding of HIV in the Genital Tract," *AIDS,* 10:1305–1315 (1996)), feces (Yolken et al., "Persistent Diarrhea and Fecal Shedding of Retroviral Nucleic Acids in Children Infected with Human Immunodeficiency Virus," *J. Infect. Dis.,* 164:61–66 (1991)), and breast milk (VandePerre et al., "Infective and Anti-Infective Properties of Breast Milk from HIV-1 Infected Women," *Lancet,* 341:914–918 (1993)). Genital secretions, feces, and breast milk have all been implicated in HIV transmission.

Particulate and filterable oral secretions capable of inhibiting HIV infection represent potential explanations for the paucity of HIV in saliva. Reports from several different groups imply that two processes are involved (Fultz, "Components of Saliva Inactivate Human Immunodeficiency Virus," *Lancet,* ii: 1215 (1986); Malamud et al., "Human Submandibular Saliva Aggregates HIV," *AIDS Res. Hum. Retroviruses,* 9:633–637 (1993); Fox et al., "Saliva Inhibits HIV-1 Infectivity," *J. Am. Dent. Assoc.,* 116:635–637 (1988); Fox et al., "Salivary Inhibition of HIV-1 Infectivity: Functional Properties and Distribution in Men, Women and Children," *J. Am. Dent. Assoc.,* 118:709–711 (1989); Archibald et al., "In Vitro Inhibition of HIV-1 Infectivity by Human Salivas," *AIDS Res. Hum. Retroviruses,* 6:1425–1432 (1990); McNeely et al., "Secretory Leukocyte Protease Inhibitor: A Human Saliva Protein Exhibiting Anti-Human Immunodeficiency Virus 1 Activity In Vitro," *J. Clin. Invest.,* 96:456–464 (1995); Malamud et al., "HIV in the Oral Cavity: Virus, Viral Inhibitory Activity, and Antibodies: A Review," *Crit. Rev. Oral. Biol. Med.,* 4:461–466 (1993); Amory et al., "The Large Molecular Weight Glycoprotein MGI, a Component of Human Saliva, Inhibits HIV-1 Infectivity," *Clin. Res.,* 40:51A (1992); Yeh et al., "Further Studies of Salivary Inhibition of HIV-I Infectivity," *J. Acquired Immune Defic. Syndr.,* 5:898–903(1992); Bergey et al., "Interaction of HIV-1 and Human Salivary Mucins," *J. Acquired Immune Defic. Svndr.,* 7:995–1002 (1994); Phillips et al., "Low Level of Cell-Free Virus Detected at High Frequency in Saliva from HIV-1 Infected Individuals," *AIDS,* 8:1011–1012 (1994)). Some studies found that whole saliva and submandibular secretions, but not parotid fluid, could sequester HIV virions (Malamud et al., "Human Submandibular Saliva Aggregates HIV," *AIDS Res. Hum. Retroviruses,* 9:633–637 (1993); Fox et al., "Saliva Inhibits HIV-1 Infectivity," *J. Am. Dent. Assoc.,* 116:635–637 (1988); Fox et al., "Salivary Inhibition of HIV-1 Infectivity: Functional Properties and Distribution in Men, Women and Children," *J. Am. Dent. Assoc.,* 118:709–711 (1989); Archibald et al., "In Vitro Inhibition of HIV-1 Infectivity by Human Salivas," *AIDS Res. Hum. Retroviruses,* 6:1425–1432 (1990); Bergey et al., "Interaction of HIV-1 and Human Salivary Mucins," *J. Acquired Immune Defic. Svndr.,* 7:995–1002 (1994)), while others identified soluble inhibitory factors capable of direct inhibition in secretions from all salivary glands, but only at very high concentrations (Yeh et al., "Further Studies of Salivary Inhibition of HIV-1 Infectivity," *J. Acquired Immune Defic. Syndr.,* 5:898–903 (1992); Phillips et al., "Low Level of Cell-Free Virus Detected at High Frequency in Saliva from HIV-1 Infected Individuals," *AIDS,* 8:1011–1012(1994)). Submandibular saliva contains sulfated polysaccharides of low (MG2) and high (MG1) molecular weights (Levine et al., "Structural Aspects of Salivary Glycoproteins," *J. Dent. Res.,* 66:436–441 (1987)), with the latter forming an anionic charge barrier to binding of the high affinity HIV receptor, CD4, to the HIV envelope glycoprotein gp120 (Amory et al., "The Large Molecular Weight Glycoprotein MGI, a Component of Human Saliva, Inhibits HIV-1 Infectivity," *Clin. Res.,* 40:51A (1992)). Secretory leukocyte protease inhibitor (SLPI), a 12 kDa protein found in whole saliva, has an effect independent of HIV binding to CD4 (McNeely et al., "Secretory Leukocyte Protease Inhibitor: A Human Saliva Protein Exhibiting Anti-Human Immunodeficiency Virus I Activity In Vitro," *J. Clin. Invest.,* 96:456–464 (1995)), albeit its significance in vivo has been questioned (Bu et al., "Secretory Leukocyte Protease Inhibitor (SLPI) does not Effectively Inhibit HIV-1 Replication," $35^{th}$ ICAAC, San Francisco, Calif., Sept. 17–20:Abst. 1142 (1995)). Fibronectin, a matrix adhesion molecule, binds directly to gp120, but was shown to inhibit infectivity only at high concentrations (Su et al., "Interaction of the Envelope Glycoprotein of Human Immunodeficiency Virus with Clq and Fibronectin Under Conditions Present in Saliva," *Mol. Immunol.,* 28:811–817 (1991)).

None of the above-cited references has positively identified the factor in saliva which is capable of inhibiting HIV infectivity. The present invention is directed to overcoming this and other deficiencies in the art.

SUMMARY OF THE INVENTION

The present invention relates to a method for suppressing infectivity of HIV. This method is carried out by contacting the HIV or a cell targeted by HIV with an effective amount of a thrombospondin ("TSP") or a TSP analog. By contacting the HIV with an effective amount of a TSP or a TSP analog, the ability of HIV to bind to its cellular target is inhibited. Similarly, by contacting the cell targeted by HIV with an effective amount of a TSP or a TSP analog, the ability of HIV to bind to its cellular target is also inhibited. Both approaches are useful in suppressing HIV infectivity.

The present invention further relates to a method of inhibiting HIV infection in a patient which includes administering a TSP or a TSP analog to a patient under conditions effective to inhibit HIV infection.

The present invention also relates to a method of blocking HIV binding to a cell targeted by HIV. This method includes contacting the HIV or the cell targeted by HIV with a TSP or a TSP analog under conditions effective to block binding of the HIV to the cell.

Because HIV is capable of spreading via sexual contact as well as non-sexual contact (e.g., surgical procedures), pharmaceutical compositions, contraceptives, and non-contraceptive prophylactic devices capable of decreasing the likelihood of HIV infection are particularly desirable. Therefore, another embodiment of the present invention relates to a contraceptive that includes a contraceptive carrier and a TSP or a TSP analog. Also encompassed by the present invention is a pharmaceutical composition that includes a pharmaceutically-acceptable carrier and a TSP or a TSP analog. A non-contraceptive prophylactic device of the present invention includes a non-contraceptive carrier and a TSP or a TSP analog.

The present invention also relates to a method of blocking the binding of a chemokine to its receptor by contacting a chemokine with a TSP or a TSP analog under conditions effective to bind the chemokine. Because chemokines are generally implicated in inflammatory states, another aspect of the present invention relates to a method of treating or preventing inflammatory states in a patient by administering an effective amount of a TSP or a TSP analog to a patient.

By demonstrating the ability of purified thrombospondin-1 ("TSP-1") to block HIV-1 infection of primary and transformed target cell lines through the binding of TSP 1 to C2 and C3 conserved regions adjoining the V3 loop of HIV-1 envelope glycoprotein gp120 or through the binding of TSP1 to the CD4 cell surface receptor, potential targets for therapeutic intervention in HIV infectivity has been identified. Previously, it has been shown that the V3 loop region of gp120 is a key determinant for the binding of this glycoprotein to its high affinity CD4 cellular receptor (Ivanhoff, L. A. et al., "V3 Loop Region of the HIV-1 Envelope Protein is Essential for Virus Infectivity," Virology, 187:423–432 (1992), which is hereby incorporated by reference). The effect of TSP1, particularly the polypeptide sequence cys-ser-val-thr-cys-gly (SEQ. ID. NO. 1), on CD4-gp120 complex formation provides a target for therapeutic intervention.

DETAILED DESCRIPTION OF THE INVENTION

The present invention relates to a method for suppressing infectivity of HIV. This process includes contacting the HIV or a cell targeted by HIV with an effective amount of a TSP or a TSP analog.

TSP1 is a trimeric sulfated glycoprotein which belongs to a family of high molecular weight extracellular matrix molecules reviewed in Bornstein, "Thrombospondins: Structure and Regulation of Expression," FASEB, 6:3290–3299 (1992); Lahav, editor, "Thrombospondin," CRC Press, (1993), which are hereby incorporated by reference. TSP1 is implicated in suppressing the infectivity of certain bacteria and protozoa, including *Staphylococcus aureus, babesia, toxoplasma, leishmania*, and the malaria sporozoite (Lahav, "The Functions of Thrombospondin and its Involvement in Physiology and Pathophysiology," *Biochim. Biophys. Acta,* 1182:1–14 (1993); Sinnis et al., "Remnant Lipoproteins Inhibit Malaria Sporozoite Invasion of Hepatocytes," *J. Exp. Med.,* 184:945–954 (1996), which are hereby incorporated by reference). Unlike other multifunctional glycoproteins, TSP1 is found in very low quantities in plasma, but is stabilized during reversible binding to other matrix molecules, resulting in markedly elevated levels at certain cell surfaces (Taraboletti et al., "Platelet Thrombospondin Modulates Endothelial Cell Adhesion, Motility, and Growth: A Potential Angiogenesis Regulatory Factor," J. Cell Biol., 111:765–772 (1990), which is hereby incorporated by reference).

TSP1 and thrombospondin-2 ("TSP2") have been shown to have a similar structure in mice (Bornstein, "Thrombospondins: Structure and Regulation of Expression," FASEB, 6:3290–3299 (1992), which is hereby incorporated by reference) and in humans (LaBell et al., "Sequence and Characterization of the Complete Human Thrombospondin 2 cDNA: Potential Regulatory Role for the 3' Untranslated Region," Genomics 17:225–229 (1993), which is hereby incorporated by reference). Human TSP1 and human TSP2 are functionally and structurally similar and have an amino acid identity which is about 54 percent (LaBell et al., "Sequence and Characterization of the Complete Human Thrombospondin 2 cDNA: Potential Regulatory Role for the 3' Untranslated Region," Genomics 17:225–229 (1993), which is hereby incorporated by reference). In addition, human TSP1 and mouse TSP1 have been shown to share a high degree of homology to one another (Bornstein, "Thrombospondins: Structure and Regulation of Expression," FASEB, 6:3290–3299 (1992), which is hereby incorporated by reference), as have human TSP2 and mouse TSP2 (LaBell et al., "Sequence and Characterization of the Complete Human Thrombospondin 2 cDNA: Potential Regulatory Role for the 3' Untranslated Region," Genomics 17:225–229 (1993), which is hereby incorporated by reference).

Figure 11:
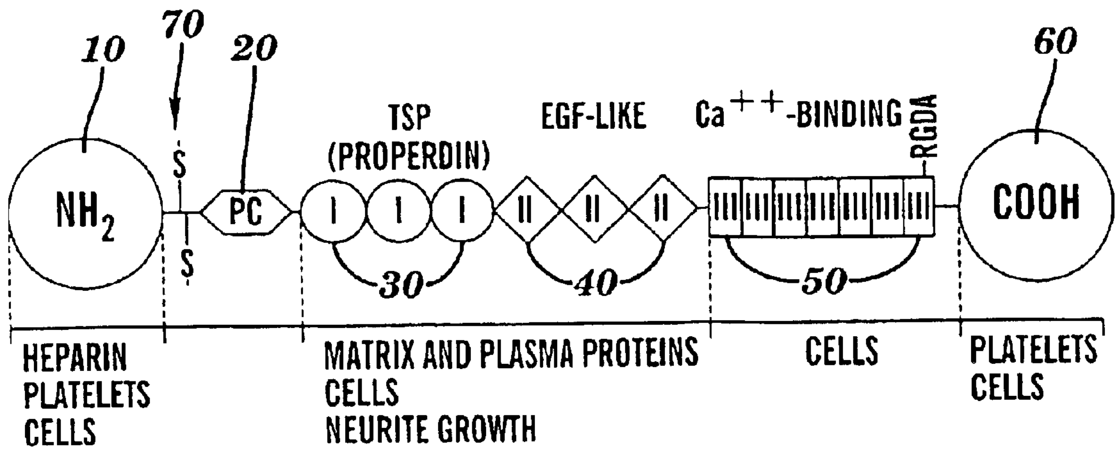
FIG. 11 is a diagram representing the structure of TSP1 and TSP2. Below each domain or region are listed some of the major interactions that have been established previously for human platelet TSP1.

Referring to FIG. 11, both TSP1 and TSP2 contain similar functional domains or regions, including an N-terminal region 10, a procollagen-homologous region 20, type I TSP repeats 30, type II TSP repeats 40, type III calcium-binding repeats 50, and a carboxy-terminal region 60 (Bornstein, "Thrombospondins: Structure and Regulation of Expression," FASEB, 6:3290–3299 (1992); Lawler et al., "The Structure of Human Thrombospondin, an Adhesive Glycoprotein with Multiple Calcium-binding Sites and Homologies with Several Different Proteins," J. Cell Biol. 103:1635–1648 (1986), which are hereby incorporated by reference). Each of these regions is addressed more fully below.

The genes encoding TSP 1 and TSP2 each contain 21 exons. Exons 1–2 of each TSP gene encode the 5' untranslatable region ("UTR") and translation start sequences, while exon 22 of each TSP gene encodes a 3' UTR. The remaining exons all encode functional regions or domains of the mature TSP 1 or TSP2.

Referring again to FIG. 11, the N-terminal region 10 of TSP1 and TSP2 includes a heparin-binding domain. This region includes two sequences of tandemly repeated basic residues that are believed to represent the specific sites which bind anionic heparin. The N-terminal region 10 can be cleaved from TSP1 or TSP2 by thermolysin or chymotrypsin.

A variable segment 70 of TSP1 and TSP2, located between the N-terminal region 10 and the procollagen-homologous region 20, contains two cysteine residues which are believed to be involved in the formation of interchain di-sulfide bridges during trimerization.

The procollagen-homologous region 20 of TSP1 and TSP2 is cysteine-rich and shares homology with the $NH_2$-propeptide of the α(I) chain of type I procollagen.

Following the procollagen-homologous region is the region containing the type I TSP repeats 30. TSP1 and TSP2 each contain three type I TSP repeats 30 having between 50–54 amino acid residues. The type I TSP repeat 30 has been found to be conserved in a number of different proteins including, among others, antistasin (Holt et al., "Properdin Binds to Sulfatide [Gal($350_4$) beta 1—1 Cer] and Has a Sequence Homology with Other Proteins That Bind Sulfated Glycoconjugates," *J. Biol. Chem.* 265:2852–2855 (1990), which is hereby incorporated by reference), proteins involved in the complement cascade such as properdin (Smith et al., "Neutron and X-ray Scattering Studies on the Human Complement Protein Properdin Provide an Analysis of the Thrombospondin Repeat," *Biochem.* 30:8000–8008 (1991), which is hereby incorporated by reference), and f-spondin (Klar et al., "F-spondin: A Gene Expressed at High Levels in the Floor Plate Encodes a Secreted Protein that Promotes Neural Cell Adhesion and Neurite Extension," *Cell* 69:95–110 (1992), which is hereby incorporated by reference). The type I repeats of TSP fall into group 1, as characterized by Smith et al., "Neutron and X-ray Scattering Studies on the Human Complement Protein Properdin Provide an Analysis of the Thrombospondin Repeat," Biochem. 30:8000–8008 (1991), which is hereby incorporated by reference, whereas the type I repeats of f-spondin fall into group 2. The type I TSP repeat 30 contains a cys-ser-val-thr-cyg-gly ("CSVTCG") motif (SEQ. ID. No. 1), which is found in both group I and group 2 repeats. This sequence has been implicated in the binding of various proteins to cells. The amino acid sequence containing the CSVTCG motif (SEQ. ID. No. 1) is also conserved between TSP1 and TSP2.

Following the type I TSP repeats is the region containing the type II TSP repeats 40, also known as EGF-like repeats. TSP1 and TSP2 each contain three type II TSP repeats 40. A role for the EGF-like domain in ligand-receptor interactions has been proposed (Appella et al., "Structure and Function of Epidermal Growth Factor-Like Regions in Proteins," FEBS Lett. 231:1–4 (1988), which is hereby incorporated by reference).

Following the type II TSP repeats is the region containing the type III calcium-binding repeats 50. Each of the type III repeats 50 contains two cysteine residues, presumably involved in a disulfide bond, and either seven or ten highly conserved asparagine, glutamine, and aspartic acid residues that could serve to complex with calcium. The type III repeats 50 are functionally related to the E/F hand of calmodulin and also have features in common with calcium-binding structures in parvalbumin and fibrinogen (Lawler et al., "The Structure of Human Thrombospondin, an Adhesive Glycoprotein with Multiple Calcium-Binding Sites and Homologies with Several Different Proteins," *J. Cell. Biol.*

103:1635–1648 (1986), which is hereby incorporated by reference). Because the structure of this region of the molecule could be sensitive to calcium ion concentration, it is possible that the interaction of TSP1 with cell-surface integrins could also be modulated by calcium (Frazier, "Thrombospondin: A Modular Adhesive Glycoprotein of Platelets and Nucleated Cells," *J. Cell Biol.* 105:625–632 (1987); Lawler et al., "Cell Attachment to Thrombospondin: The Role of ARG-GLY-ASP, Calcium, and Integrin Receptors," *J. Cell Biol.* 107:2351–2361 (1988), which are hereby incorporated by reference).

The carboxy-terminal region 60 is highly conserved between TSP 1 and TSP2. This region has been implicated for involvement with platelets, melanoma cells, keratinocytes, and squamous cell carcinoma cells (reviewed in Prater et al., "The Properdin-like Type I Repeats of Human Thrombospondin Contain a Cell Attachment Site," *J. Cell Biol.* 112:1031–1040 (1991), which is hereby incorporated by reference).

Figure 1:
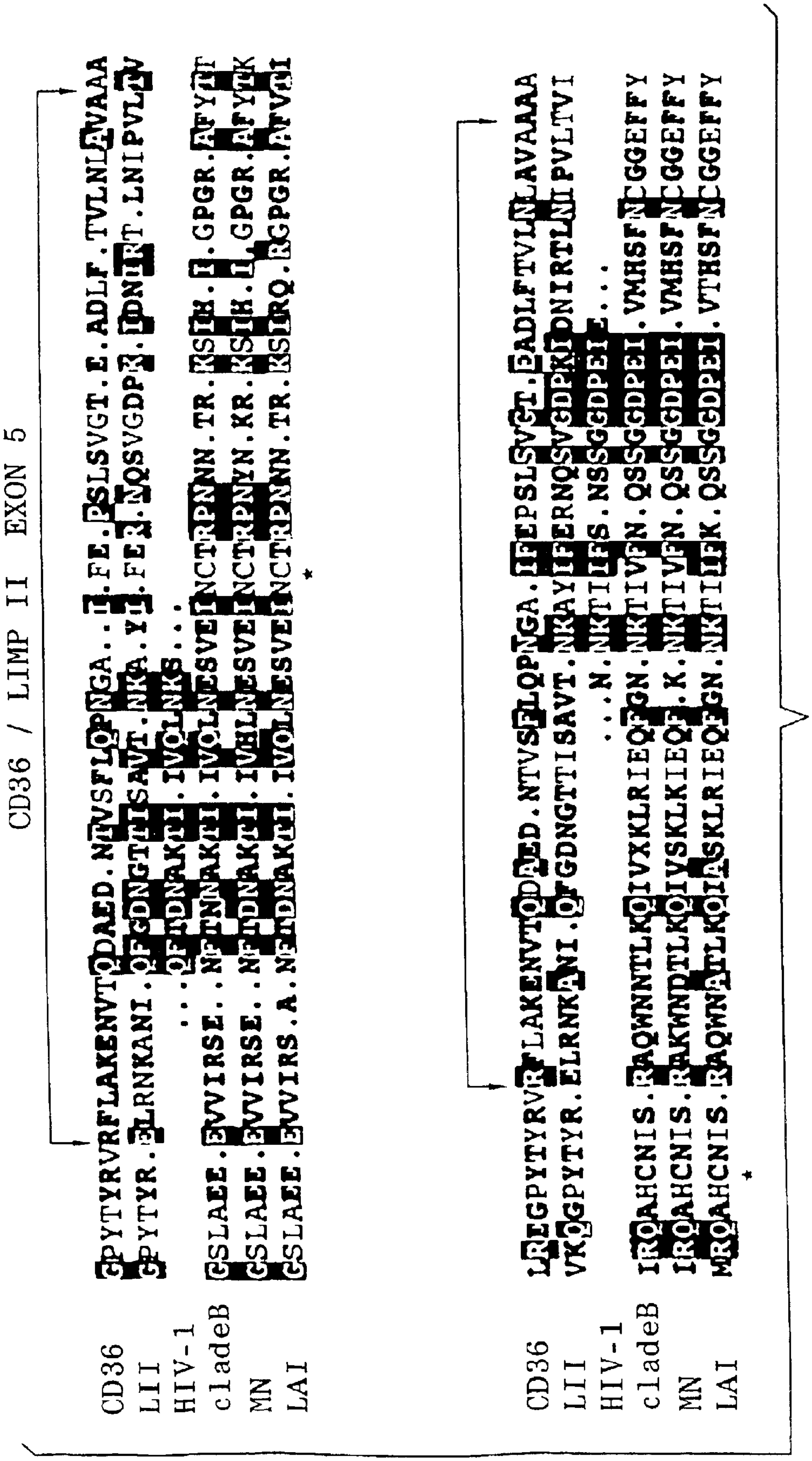
FIG. 1 is an amino acid sequence alignment of CD36/LIMPII TSP binding motifs with homologous sequences in HIV-I gp120. Results of a pattern-based Blast enhanced alignment utility search that matched a split motif in gp120 domains C2 (top) and C3 (bottom). In the upper alignment, a polypeptide of human CD36 (aa 4–60 of SEQ. ID. NO. 5) is aligned with a human LIMP II polypeptide (aa 4–60 of SEQ. ID. NO. 6), a polypeptide of HIV-1 gp120 from isolate U37041 (SEQ. ID. NO. 7), an HIV-1 clade B consensus (SEQ. ID. NO. 8), a polypeptide of HIV-1 gp120 from isolate MN (SEQ. ID. NO 9), and a polypeptide of HIV-1 gp120 from isolate LAI (SEQ. ID. NO. 10). In the lower alignment, a polypeptide of human CD36 (SEQ. ID. NO. 5) is aligned with a human LIMP II polypeptide (SEQ. ID. NO. 6), a polypeptide of HIV-1 gp120 from isolate U37041 (SEQ. ID. NO. 11), an HIV-1 clade B consensus (SEQ. ID. NO. 12), a polypeptide of HI-I gp120 from isolate MN (SEQ. ID. NO. 13), and a polypeptide of HIV-1 gp120 from isolate LAI (SEQ. ID. NO. 14). Asterisks (*) indicate disulfide-bonded cysteine residues of the V3 loop. The brackets above alignments show boundaries of CD36 Exon 5 coding region (CD36 aa 95–143). Amino acids identical between either CD36 or LIMPII and HIV-I gp120 are highlighted. Bold residues represent conservative substitutions according to the following groups: basic (KRH), acidic (DE), charged (KRH, DE), aromatic (YRW), hydroxy (STY), aliphatic (AG), nonpolar/branched (IVL), hydrophobic (AGP, IVL, FM), polar/hydrophilic (ST, KRH, DNEQ, CWY), X=any aa, period=gap. GenBank™/EMBL accession numbers: huCD36, M24795; huLIMPII, D12676; HIV-1 partial sequence of isolate U37041; HIV-1 clade B consensus, M and LAI isolate sequences were retrieved from the WHO HIV Sequence Database.

The presence of an evolutionary conserved TSP 1 binding domain, termed CLESH-1, was recently established as functional in at least two members of the CD36 gene family, cell surface adhesion receptor CD36 (Pearce et al., "Recombinant GST/CD36 Fusion Proteins Define a Thrombospondin Binding Domain: Evidence for a Single Calcium-Dependent Binding Site on CD36," *J. Biol. Chem.,* 270:2981–2986 (1995), which is hereby incorporated by reference) and lysosomal integral membrane protein II ("LIMPII") (Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9):4855–63 (1998), which is hereby incorporated by reference). Referring to FIG. 1, the CLESH-1 motif appears within the bracketed portions of each sequence alignment.

TSP can be isolated from tissue or fluid samples (e.g., plasma) by established techniques described in Silverstein et al., "Platelet Thrombospondin Forms a Trimolecular Complex with Plasminogen and Histadine-Rich Glycoprotein," *J. Clin. Invest.* 75:2065–2073 (1985), which is hereby incorporated by reference. Preferably the TSP is produced in purified form, i.e., preferably at least about 80% pure, more preferably at least 90% pure, and most preferably at least about 95% pure. Purified TSP1 derived from human platelets is also commercially available from Sigma Chemical Co. (St. Louis, Mo.).

TSP can also be prepared using recombinant techniques. DNA molecules encoding TSP1 (Wolf et al., "Structure and Chromosomal Localization of the Human Thrombospondin Gene," Genomics 6:685–691 (1990), which is hereby incorporated by reference) and TSP2 (LaBell et al., "Sequence and Characterization of the Complete Human Thrombospondin 2 cDNA: Potential Regulatory Role for the 3' Untranslated Region," Genomics 17:225–229 (1993), which is hereby incorporated by reference) have been isolated and described. Once obtained, the DNA molecule encoding TSP can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. Transformed host cells capable of producing recombinant TSP can be grown in culture and the expressed TSP can be isolated from the growth medium using conventional protein separation techniques.

Suitable TSP analogs are fragments of TSP. TSP analogs can be obtained following cleavage of TSP by proteases. Exemplary proteases include chymotrypsin, thermolysin, and thrombin (Dixit et al., "Isolation and Characterization of a Heparin-binding Domain from the Amino Terminus of Platelet Thrombosis," *J. Biol. Chem.* 259:10100–10105 (1984); Mumby et al., Interactions of Thrombospondin with Extracellular Matrix Proteins: Selective Binding to Type V Collagen," *J. Cell Biol.* 98:646–652 (1984), which are hereby incorporated by reference). Once fragments of TSP are produced, they can be isolated using immunoselective techniques (Dixit et al., "Monoclonal Antibodies that Recognize Calcium-dependent Structures of Human Thrombospondin. Characterization of Mapping Their Epitopes," *J. Biol. Chem.* 261:1962–1968 (1986); Galvin et al., "Mapping of Epitopes for Monoclonal Antibodies Against Human Platelet Thrombospondin with Electron Microscopy and High Sensitivity Amino Acid Sequencing," *J. Biol. Chem.* 101;1434–1441 (1985), which are hereby incorporated by reference), HPLC, or gel electrophoresis.

Alternatively, chemical synthesis can be used to prepare TSP peptides (TSP analogs) according to the methods of Guo et al., "Heparin-binding Peptides from the Type I Repeats of Thrombospondin. Structural Requirements for Heparin Binding and Promotion of Melanoma Cell Adhesion and Chemotaxis," *J. Biol. Chem.* 267:19349–19355 (1992) and Guo et al., "Heparin- and Sulfatide-binding Peptides from the Type I Repeats of Human Thrombospondin Promote Melanoma Cell Adhesion." Proc. Natl. Acad. Sci. USA 89:3040–3044 (1992), both of which are hereby incorporated by reference. Basically, this approach involves using standard Merrifield solid-phase synthesis protocols and t-butoxycarbonyl chemistry. Resulting peptides can be analyzed by reverse-phase HPLC and/or mass spectrometry.

Other conventional peptide synthesis schemes, such as liquid-phase protocols, can also be employed.

TSP analogs can also be produced using conventional recombinant technologies as described above.

Exemplary TSP analogs include an N-terminal region of TSP (e.g., TSP1 and TSP2), a procollagen-homologous region of TSP (e.g., TSP1 and TSP2), a type I repeat of TSP (e.g., TSP1 and TSP2), a type II repeat of TSP (e.g., TSP1 and TSP2), a calcium-binding domain of TSP (e.g., TSP1 and TSP2), a carboxy-terminal region of TSP (e.g., TSP1 and TSP2), and TSP domains which bind to an HIV gp120 envelope protein. A preferred TSP analog is a polypeptide containing a CSVTCG amino acid sequence (SEQ. ID. No. 1). Depending upon the intended use of the TSP analogs, the TSP analogs can be defined as TSP domains which bind to an HIV gp120 envelope protein, TSP domains which bind to a CD4 receptor on a cell, or TSP domains which bind to a chemokine (e.g., RANTES).

Other suitable TSP analogs may include molecules, such as fusion proteins, containing TSP or any one of the above-identified TSP analogs. Thus, the fusion protein can contain one or more domains/regions of TSP or the CSVTCG amino acid sequence (SEQ. ID. No. 1). Fusion proteins can be prepared by ligating two DNA molecules together, one of which encodes TSP or the TSP analog and the other of which encodes a stable host protein. Suitable host proteins include, among others, glutathione-S-transferase (Frangioni et al., "Solubilization and Purification of Enzymatically Active Glutathione-S-Transferase (pGEX) Fusion Proteins," *Analyt. Biochem.,* 210:179–187 (1993), which is hereby incorporated by reference) and maltose-binding protein (Rodriguez et al., "Improved Factor Xa Cleavage of Fusion Proteins Containing Maltose Binding Protein," *Biotechniques* 18(2):238, 241–243 (1995), which is hereby incorporated by reference). The two DNA molecules must be ligated in a manner which allows their proper expression. A number of efficient expression schemes for preparing fusion proteins have been developed and are well known in the art. According to one approach the fusion protein is prepared with a protease cleavage site intermediate the host protein and the TSP or TSP analog, such that the TSP or TSP analog can be removed from the host protein by, for example, proteolytic cleavage following isolation of the fusion protein. A linker or spacer peptide may also be included to promote proteolytic cleavage (Polyak et al., "Introduction of Spacer Peptides N-terminal to a Cleavage Recognition Motif in Recombinant Fusion Proteins Can Improve Site-specific Cleavage," *Protein Ens.* 10(6):615–619 (1997), which is hereby incorporated by reference). A number of suitable proteases (e.g., factor Xa, chymosin, trypsin, etc.) and their protease-specific cleavage sites are known in the art, and others continually being identified.

The complete nucleotide sequence of the HIV viruses have been reported by several investigators (Ratner et al., "Complete Nucleotide Sequence of the AIDS virus, HTLV-III," *Nature* 313:277–84 (1985); Muesing et al., "Nucleic Acid Structure and Expression of the Human AIDS/lymphadenopathy Retrovirus," Nature 313:450–458 (1985); Wain-Hobson et al., "Nucleotide Sequence of the AIDS Virus, LAV," Cell 40:9–17 (1985), which are hereby incorporated by reference). The RNA of the HIV-1 and HIV-2 viruses possess the following gene regions: so-called long terminal repeats at each end of the genome, gag, pol, env, and nef. The gag gene encodes the core proteins p24 and p17. The pol gene encodes the reverse transcriptase, RNAse H, and integrase. The gene nef encodes a protein having a regulatory function. The env gene encodes the glycoproteins of the viral coat, namely gp41 and gp120. The env gene has been associated particularly with antigenicity and infectivity. However, the env portion is also known to have regions which are highly divergent between different strains.

The HIV virus has been shown to bind to a cell surface receptor known as the CD4 or T4 region, which is present on the various cells susceptible to HIV infection, including T lymphocytes and macrophages (Shaw et al., "Molecular Characterization of Human T-Cell Leukemia (Lymphotrophic) Virus Type III in the Acquired Immune Deficiency Syndrome," *Science* 226:1165–1171 (1984), which is hereby incorporated by reference). In addition, HIV co-receptors have been implicated in HIV entry inside a cell, because the primary cell surface receptor, CD4, is often by itself insufficient to enable viral entry. HIV co-receptors are cell surface proteins that HIV uses to dock onto its cellular targets. Thus, a cooperative interaction between CD4, a co-receptor, and HIV gp120 envelope protein must occur. There are presently thirteen known HIV co-receptors, including CCR5, CXCR4, and CCR2B (Balter, "AIDS Researchers Negotiate Tricky Slopes of Science," *Science* 280:825–826 (1998), which is hereby incorporated by reference).

According to one embodiment, the method for suppressing HIV infectivity is carried out by contacting the HIV with an effective amount of TSP or the TSP analog. By doing so, the process of the present invention suppresses the ability of HIV to infect a host organism by blocking its ability to bind to its cellular target (e.g., T lymphocytes and macrophages). Specifically, the TSP or TSP analog are administered in a manner effective to contact the HIV gp120 envelope protein. Because the gp120 envelope protein is necessary for the binding of HIV to its cellular target, TSP or the TSP analog can inhibit or interfere with HIV binding to its cellular target. It is believed that the inhibition or interference with HIV binding to its cellular target results from the TSP or TSP analog binding to the gp120 envelope protein in a manner which either prevents HIV from binding to the cell surface receptor (e.g., CD4) or co-receptor (e.g., chemokine receptor CCR5), or causes steric interference between the functional domains of the gp120 envelope protein and the receptor/co-receptor.

According to another embodiment, the method is carried out by contacting a cell targeted by HIV with an effective amount of a TSP or TSP analog. Specifically, the TSP or TSP analog is administered in a manner effective to contact the CD4 receptor on a cell. Because the CD4 receptor is necessary for the binding of HIV to its cellular target, TSP or the TSP analog can inhibit or interfere with HIV binding to its cellular target.

According to another embodiment, the method is carried out by both contacting the HIV with an effective amount of TSP or a TSP analog and contacting the cell targeted by HIV with an effective amount of TSP or a TSP analog. Thus, the ability of HIV to bind and recognize its cellular target as well as the ability of the CD4 receptor (or the co-receptor) to recognize HIV can both be affected to further suppress HIV infectivity.

TSP or the TSP analog can be administered orally or intraorally, parenterally, subcutaneously, intravenously, intramuscularly, intraperitoneally, by intranasal instillation, by intracavitary or intravesical instillation, intravaginally or intrarectally (e.g., by suppository, ointment, etc.) intrasynovially, intraocularly, intrarterially, intralesionally, or by application to mucous membranes, such as, that of the nose, throat, and bronchial tubes via inhalation or otherwise (e.g., using an aerosol or lavage). When TSP or the TSP analog are used in accordance with the methods of the present invention concerning HIV infectivity or binding as described herein, the preferred route for administration is intraorally, intrarectally, or intravaginally.

TSP and the TSP analog can each be administered alone, with a spermicide, or with pharmaceutically or physiologically acceptable carriers, excipients, or stabilizers, in solid or liquid form, such as tablets, capsules, powders, solutions, suspensions, or emulsions, which may also include microcapsules or liposomes.

Thus, another aspect of the present invention relates to a pharmaceutical composition which includes a pharmaceutically-acceptable carrier in combination with TSP or the TSP analog. The pharmaceutical composition can also include additives commonly used for pharmaceutical preparations, if desired, such as excipients, stabilizers, antiseptics, solubilizers, wetting agents, emulsifying agents, lubricants, sweetening agents, coloring agents, flavors, antioxidants, and the like.

The solid unit dosage forms can be of the conventional type. The solid form can be a capsule, such as an ordinary gelatin type which includes TSP or the TSP analog and a pharmaceutical carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

TSP and the TSP analog can also be administered topically in the form of a solution or suspension of these materials in a physiologically acceptable diluent with a pharmaceutical carrier. Such carriers include sterile liquids, such as water and oils, with or without the addition of a surfactant and other pharmaceutically and physiologically acceptable carriers, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, TSP and the TSP analog can be prepared in solution or suspension and packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

A preferred formulation for the pharmaceutical composition of the present invention contains TSP1 or TSP2 in the pharmaceutically-acceptable carrier.

Another preferred formulation for the pharmaceutical composition of the present invention contains a TSP analog in the pharmaceutically-acceptable carrier.

Because of the possibility for transmission of HIV from an infected person to another via oral exchange, it is preferable for the pharmaceutical composition to be an oral hygiene composition. Thus, the oral hygiene composition is a pharmaceutical composition which contains a carrier that is a pharmaceutically-acceptable topical oral carrier. Suitable topical oral carriers include a toothpaste, a mouthwash or other oral rinse, a lozenge, and a gum. Details with regard to formulating oral hygiene compositions can be found in, for example, U.S. Pat. No. 5,686,064 to Gaffar et al., U.S. Pat. No. 5,672,351 to Chikindas, and U.S. Pat. No. 5,578,295 to Francis et al., which are hereby incorporated by reference. Other processes for formulating oral hygiene compositions are well known in the art.

Because of the possibility for transmission of HIV from an infected person to another via sexual contact, it is also desirable to provide a contraceptive capable of suppressing HIV infectivity. Thus, another aspect of the present invention relates to a contraceptive that includes a contraceptive carrier and a TSP or a TSP analog.

The contraceptive carrier can be a contraceptive composition or a contraceptive device.

Suitable contraceptive compositions include contraceptive foams, jellies, lubricants, and spermicides. The contraceptive composition can be a pharmaceutical composition of the present invention. Details with regard to the formulation of contraceptive compositions, such as contraceptive foams, jellies, lubricants, spermicides, and the like, are generally known to those skilled in the art and are described in, for example, U.S. Pat. No. 5,595,980 to Brode et al., which is hereby incorporated by reference.

Suitable contraceptive devices include sponges, cervical diaphragms and caps, intravaginal devices, and condoms. Contraceptive devices containing molecules which include TSP or TSP analogs (e.g., the CSVTCG amino acid sequence of SEQ. ID. No. 1) can be prepared by methods described in, for example, U.S. Pat. No. 5,571,567 to Shah et al., which is hereby incorporated by reference. Further details regarding contraceptive formulation and manufacture can be found in U.S. Pat. No. 5,545,615 to Maraganore and U.S. Pat. No. 5,527,534 to Myhling, which are hereby incorporated by reference. Other processes for preparing contraceptive formulations and contraceptive devices are well known in the art.

In addition, in some instances, a contraceptive composition in accordance with the present invention can be used in combination with a contraceptive device of the present invention. For example, a condom or sponge of the present invention can contain a spermicide of the present invention.

Because of the possibility for transmission of HIV from an infected person to another via non-sexual contact (e.g., surgical procedures) as well as sexual contact, it is also desirable to provide a non-contraceptive prophylactic device capable of suppressing HIV infectivity. Thus, another aspect of the present invention relates to a non-contraceptive prophylactic device that includes a non-contraceptive carrier and a TSP or a TSP analog.

The non-contraceptive carrier can be a carrier other than the contraceptive carriers described above. Specifically, it is intended that the non-contraceptive carrier is a type of physical barrier. Thus, suitable non-contraceptive carriers can take any form or configuration, but, preferably, they are in the, form of a surgical glove, a dental dam, or an oral dam. Non-contraceptive carriers for this aspect of the present invention can be prepared by methods described in, for example, U.S. Pat. No. 5,571,567 to Shah et al., which is hereby incorporated by reference. Suitable surgical gloves can be of any conventional design, including, but not limited to, surgical gloves of the type disclosed in U.S. Pat. No. 5,317,759 to Pierce, U.S. Pat. No. 5,817,433 to Darras, and U.S. Pat. No. 4,901,372 to Pierce, which are hereby incorporated by reference. Suitable dental darns can be of any conventional design, including, but not limited to, dental dams of the type disclosed in U.S. Pat. No. 4,721,465 to Barasz and U.S. Pat. No. 3,662,466 to McConville. Suitable oral dams also can be of any conventional design, including, but not limited to, oral dams of the type disclosed in U.S. Pat. No. 4,949,731 to Harding and U.S. Pat. No. 5,388,592 to Williams, which are hereby incorporated by reference.

In some instances, it may be possible to utilize a pharmaceutical composition of the present invention together with a non-contraceptive prophylactic device of the present invention.

Another aspect of the present invention relates to a method of inhibiting HIV infection in a patient. This method includes administering TSP or a TSP analog to the patient under conditions effective to inhibit HIV infection.

To inhibit HIV infection, the TSP or TSP analog should be administered prior to and, optionally, immediately following exposure to the HIV. To administer the TSP or TSP analog, a pharmaceutical composition of the present invention, a contraceptive of the present invention, a non-contraceptive prophylactic device of the present invention, or combinations thereof can be used.

It will be appreciated that the actual amount of the TSP or TSP analog to be administered according to the present invention will vary according to the particular compound, the particular composition, and the particular mode of administration. Many factors that may modify the action of the TSP or TSP analog can be taken into account by those skilled in the art; e.g., time of administration, route of administration, condition of the subject, drug combinations, etc. Optimal administration rates for a given set of conditions can be ascertained by those skilled in the art using conventional dosage administration tests.

When this method of the present invention is carried out by administering TSP to the patient, it is preferable that the TSP is TSP1 or TSP2. When this method of the present invention is carried out by administering a TSP analog to the patient, a preferred TSP analog is the polypeptide containing a CSVTCG amino acid sequence (SEQ. ID. No. 1). Because the threat of spreading HIV is greatest via oral, vaginal, or rectal routes, it is preferable that the administration of the TSP or TSP analog is intraorally, intravaginally, or intrarectally.

Still another aspect of the present invention relates to a method of blocking HIV binding to a cell targeted by HIV. This method includes contacting HIV or the cell targeted by HIV with TSP or a TSP analog under conditions effective to block binding of the HIV to the cell.

When this method of the present invention is carried out by contacting HIV with TSP, it is preferable that the TSP is TSP1 or TSP2. When this method of the present invention is carried out by contacting HIV with a TSP analog, a preferred TSP analog is the polypeptide containing a CSVTCG amino acid sequence (SEQ. ID. No. 1). Regardless of whether the TSP or TSP analog is used to contact the HIV, the TSP or TSP analog is administered in a manner effective to contact the HIV gp120 envelope protein. By contacting the gp120 envelope protein, the HIV is effectively blocked from binding to its cellular target as described above.

When this method of the present invention is carried out by contacting the cell with TSP, it is preferable that the TSP is TSP1 or TSP2. When this method of the present invention is carried out by contacting the cell with a TSP analog, a preferred TSP analog is the polypeptide containing a CSVTCG amino acid sequence (SEQ. ID. No. 1). Regardless of whether the TSP or TSP analog is used to contact the cell, the TSP or TSP analog is administered in a manner effective to contact the CD4 receptor. By contacting the CD4 receptor, the HIV is effectively blocked from binding to its cellular target as described above.

It has also been discovered that TSP or TSP analogs can affect the activity of certain types of immunomodulatory proteins which are chemotactic cytokines, called "chemokines." Chemokines are small molecular weight immune ligands which are chemoattractants for leukocytes, such as neutrophils, basophils, monocytes, and T cells. There are two major classes of chemokines, an α-class and a β-class. Chemokines in each class contain four conserved cysteine residues that form disulfide bonds in the tertiary structure of the proteins. The α-class is characterized by C-X-C motifs (where X is any amino acid) and includes IL-8, CTAP-III, a gro/MGSA, and ENA-78. The P-class is characterized by C—C motifs and includes MCP-1, MIP-1α, MIP-1β, and the regulated on activation normal T expressed and secreted protein ("RANTES"). Thus, the designations of the classes are according to whether an intervening residue spaces the first two cysteines in the motif. In general, α-chemokines (C-X-C) are chemoattractants for neutrophils but not monocytes, whereas β-chemokines (C—C) appear to attract monocytes but not neutrophils. Recently, a third group of chemokines, the "C" group, was designated by the discovery of a new protein called lymphotactin (Kelner et al., "Lymphotactin: A Cytokine That Represents a New Class of Chemokine," *Science* 266:1395–1399 (1994), which is hereby incorporated by reference). The chemokine family is believed to be critically important in the direction of lymphocytes and monocytes into sites of inflammation.

In particular, it has been discovered that TSP and TSP analogs are capable of binding to chemokines, particularly to the chemokine RANTES. RANTES is important for two reasons. First, RANTES is involved in inflammation (Barnes et al., "Polyclonal Antibody Directed Against Human RANTES Ameliorates Disease in the Lewis Rat Adjuvant-induced Arthritis Model," *J. Clin. Invest.* 101(2) :2910–2919 (1998), which is hereby incorporated by reference). Second, the natural receptor for RANTES is CCR5, the principal co-receptor that permits HIV to bind to and infect cells.

Therefore, a further aspect of the present invention relates to a method of treating or preventing inflammatory states in a patient. This method includes administering an effective amount of TSP or a TSP analog to the patient. When TSP is administered to the patient in accordance with this process of the present invention, it is preferred that the TSP is TSP1 or TSP2. When a TSP analog is administered to the patient in accordance with this process of the present invention, a preferred TSP analog is the polypeptide containing a CSVTCG amino acid sequence (SEQ. ID. No. 1).

Specific conditions in which TSP or TSP analogs of the present invention may have therapeutic value would include situations in which an undesirable immune response has occurred, including, but not limited to, autoimmune diseases such as insulin-dependent diabetes, Goodpasture's syndrome, pemphigus and pemphigoid, primary biliary cirrhosis, ulcerative colitis, rheumatoid arthritis, sclerodermna, mixed connective tissue disease and lupus erythematosus; graft versus host disease; septic shock; reperfusion injury (including injury subsequent to myocardial or cerebral infarction); atherosclerosis; asthma; and inflammatory lung disease.

Patients which can be treated according to this aspect of the present invention include any mammal, such as a mouse, a rat, a dog, or a human. In particular, administration of the TSP or TSP analog to humans suffering from various inflammatory states, such as those described above, is contemplated. TSP or TSP analogs of the present invention can be administered by any suitable and accepted route of drug administration, including those described above. Moreover, TSP or TSP analogs can be administered as a component in a pharmaceutical composition of the present invention. When prepared for such use, pharmaceutical compositions of the present invention can also contain other anti-inflammatory compounds and/or materials commonly used in pharmaceutical formulations.

Yet another aspect of the present invention relates to a method of blocking the binding of a chemokine to its receptor. This method includes contacting a chemokine with a TSP or a TSP analog under conditions effective to bind the chemokine. The binding of the chemokine is believed to interfere with its affinity for (i.e., its ability to bind) its receptor.

When TSP is used to contact the chemokine in accordance with this process of the present invention, it is preferred that the TSP is TSP1 or TSP2. When a TSP analog is used to contact the chemokine in accordance with this process of the present invention, a preferred TSP analog is the polypeptide containing a CSVTCG amino acid sequence (SEQ. ID. No. 1).

This method of the present invention is particularly effective when the chemokine to be bound by the TSP or TSP analog is a P-chemokine and the corresponding receptor is a β-chemokine receptor. A chemokine which is effectively bound by TSP or TSP analogs of the present invention is RANTES. Other chemokines of the RANTES family are expected to be effectively blocked as well. Thus, the chemokine receptor which is most effectively blocked against RANTES binding is a RANTES receptor, particularly a CCR5 receptor.

EXAMPLES

The following examples are provided to illustrate embodiments of the present invention but are by no means intended to limit its scope.

Example 1

Methodology

Protein Sequence Analysis and Homology Search

Deduced amino acid sequences encoded by Exon 5 of CD36 or homolog LIMPII (FIG. 1) that contain previously characterized TSP1 binding motifs (Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9):4855–63 (1998), which is hereby incorporated by reference) were used as query for a BLAST Enhanced Alignment Utility search ("BEAUTY") (Worley et al., "BEAUTY: An Enhanced BLAST-Based Search Tool that Integrates Multiple Biological Information Resources Into Sequence Similarity Search Results," *Genome Res.,* 5:173–184 (1995), which is hereby incorporated by reference), which incorporates Pattern-Induced Multiple Alignment ("PIMA") (Smith et al., "Pattern-Induced Multi-Sequence Alignment (PIMA) Algorithm Employing Secondary Structure-Dependent Gap Penalties for Comparative Protein Modelling," *Protein Ens.,* 5:35–41 (1992), which is hereby incorporated by reference) sequence family clusters, conserved cluster domains and PROSITE annotated libraries (Bairoch, "The PROSITE Dictionary of Sites and Patterns, its Current Status," *Nuci. Acids Res.,* 21:3097–3103 (1993), which is hereby incorporated by reference). HIV-1 consensus and subtype sequence alignments were retrieved from the Los Alamos Sequence Database.

Preparation of TSP1

Human platelet-rich plasma was obtained from the NY Blood Center. Human thrombin was from Boeringer-Mannheim (Indianapolis, Ind.). Purified human calcium-replete TSP1 was prepared from releasate of thrombin-activated washed platelets as described previously (Pearce et al., "Recombinant GST/CD36 Fusion Proteins Define a Thrombospondin Binding Domain: Evidence for a Single Calcium-Dependent Binding Site on CD36," *J. Biol. Chem.,* 270:2981–2986 (1995); Silverstein et al., "Platelet Thrombospondin Forms a Trimolecular Complex with Plasminogen and Histadine-Rich Glycoprotein," *J. Clin. Invest.* 75:2065–2073 (1985), which are hereby incorporated by reference). Dot blot analysis with monoclonal antibodies (mAb) to fibronectin and vitronectin (Calbiochem, La Jolla, Calif.) showed no reactivity. Endotoxin content was monitored by the Limulus amoebocyte lysate test, and was <1 U/μg protein. Polyclonal rabbit anti-TSP antisera and murine anti-TSP+2 mAbs 11.4 and 45.2 were prepared and characterized as reported (Silverstein et al., "Thrombospondin Binds to Monocytes-Macrophages and Mediates Platelet-Monocyte Adhesion," *J. Clin. Invest.,* 79:867–874 (1987); Pearce et al., "A Carboxy Terminal Truncation Mutant of CD36 is Secreted and Binds Thrombospondin: Evidence for a Single Transmembrane Domain," *Blood,* 84:384–389 (1994), which are hereby incorporated by reference).

Purified Fusion Proteins and Peptides

Characterization of glutathione-S-transferase ("GST") fusion proteins derived from CD36 or CD36 homolog LIMPII are reported elsewhere (Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9):4855–63 (1998), which is hereby incorporated by reference), and are numbered to indicate encoded amino acids. CFP67–157 and LFP75–155 contain functionally homologous minimal TSP1 binding domains (CD36 aa93–120) (Pearce et al., "Recombinant GST/CD36 Fusion Proteins Define a Thrombospondin Binding Domain: Evidence for a Single Calcium-Dependent Binding Site on CD36," *J. Biol. Chem.,* 270:2981–2986 (1995), which is hereby incorporated by reference) while CFP298–439 and LFP156–243 represent downstream sequences. A truncation mutant LFP75–78 was used as an additional GST1 control. Large-scale production and purification of soluble fusion protein followed the method of Frangioni and Neel (Frangioni et al., "Solubilization and Purification of Enzymatically Active Glutathione-S-Transferase (pGEX) Fusion Proteins," *Analyt. Biochem.,* 210:179–187 (1993), which is hereby incorporated by reference). For some experiments, LIMPII peptide (L75–155) was cleaved from the GST moiety with coagulation Factor Xa (Boehringer Mannheim, Indianapolis, Ind.), and purified by size exclusion chromatography (Centricon 10; Amicon, Beverly, Mass.). TSP1 synthetic peptides were from Chiron Mimotopes (Australia). Recombinant baculovirus-expressed HIV envelope glycoprotein gp160 (gp120 non-covalently linked to transmembrane component gp41) was derived from HIV-1 isolate IIIB (IntraCel Corp., Cambridge, Mass.). The following purified recombinant proteins were provided by the NIH AIDS Research and Reference Reagent Program: baculovirus-expressed HIV-1 gp120 derived from LAV and MN isolates, CHO cell-expressed soluble CD4, and HIV-1MN env synthetic peptides.

Solid Phase Binding Assays

In vitro binding experiments were performed as described previously for TSP1 binding to CD36 and LIMPII (Pearce et al., "Recombinant GST/CD36 Fusion Proteins Define a Thrombospondin Binding Domain: Evidence for a Single Calcium-Dependent Binding Site on CD36," *J. Biol. Chem.,* 270:2981–2986 (1995); Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9):4855–63 (1998), which are hereby incorporated by reference). Briefly, TSP1 (5–10 μg/ml) or fusion proteins and peptides (10–20 μg/ml) were immobilized on detachable 96-well microtiter plate strips (Immulon-4 Remov-a-well, Dynatech Laboratories, Inc.), by overnight incubation at 4° C. in carbonate buffer (100 mM $Na_2CO_3$/1 mM $MgCl_2$/0.02% $NaN_3$, pH 9.8). Washed wells were blocked with 0.5% bovine serum albumin ("BSA"), then incubated in triplicate with soluble radiolabeled ligand for 2.5 hours at 37° C. After extensive washing in 50 mM Tris pH 7.5, 150 mM NaCl, 0.5% Tween-20 (TBS-Tween), bound radioactivity was quantified by gamma counter. Radiolabeling was performed with $Na[^{125}I]$ (Amersham Life Science Inc., Arlington Heights, Ill.) using immobilized chloramine T (Iodo-beads™; Pierce Chemical Co., Rockford, Ill.) (Silverstein et al., "Thrombospondin: A Versatile Multifunctional Glycoprotein," *Atherosclerosis,* 6:245 (1986); MacGregor et al., "Rapid Purification and Partial Characterization of Human Platelet Glycoprotein IIIb, " *J. Biol. Chem.,* 264:501–506 (1989), which are hereby incorporated by reference). Specific activity of $Na[^{125}I]$ was determined for each experiment, ranging from 0.06–1.0 $\mu$Ci/$\mu$g. Specific binding was determined as quenchable in the presence of excess unlabeled ligand, above background binding to BSA-coated wells.

Immunohistochemistry

Thin tissue sections of oral mucosa autopsy specimens were processed as described (Hajjar et al., "Lipoprotein (a) Modulation of Endothelial Cell Surface Fibrinolysis and its Potential Role in Atherosclerosis," *Nature,* 339:303–305 (1989), which is hereby incorporated by reference). Formalin-fixed paraffin-embedded sections were de-waxed, pronase treated, and permeabilized in Triton X-100. Endogenous peroxidase activity was blocked by treatment with a 3% solution of $H_2O_2$ for 30 minutes. Slides were pre-incubated with normal human serum for 1 hour at 22° C., then incubated overnight at 4° C. with 1:1000 dilutions of either polyclonal rabbit anti-TSP1/TSP2, or pre-immune rabbit serum. After a brief blocking step with normal goat serum, successive rinses in PBS were performed between incubations with a 1:250 dilution of biotinylated goat anti-rabbit IgG (Dako, Carpenteria, Calif.), followed by avidin-biotin-peroxidase complex (Dako). Peroxidase deposition was visualized with 3,3'-diaminobenzidine tetrachloride. Samples were rinsed in distilled water, counterstained with hematoylin, and viewed by light microscopy.

Quantitative Immunodetection of TSP

A sandwich enzyme-linked immunosorbent assay ("ELISA") was used to measure levels of TSP in saliva and cell culture supernatants. Polystyrene 96-well microtiter plates (Falcon, Oxnard, Calif.) were coated overnight at 4° C. with 50 $\mu$g/well of 5 $\mu$g/ml anti-TSP1 mAb 45.2 in carbonate buffer, pH 9.6. Plates were extensively washed with carbonate buffer, then blocked with 1% BSA in TBS-Tween. This was followed by incubating 50 $\mu$l of sample diluted 1:16 in TBS-Tween for 2 hours at 37° C., followed by alkaline-phosphatase-conjugated goat anti-rabbit IgG (Kirkegaard & Perry Labs ("KPL"), Gaithersberg, Md.). Washed plates were developed with 100 $\mu$l/well of 1 mg/ml p-nitrophenyl phosphate in 50 mM carbonate buffer, pH 9.6 (KPL), incubated for 30 minutes at 37° C., and absorbance at 410 nm measured using a Microtek plate reader. Quantitation was estimated relative to a standard curve constructed using purified TSP1 diluted in TBS-Tween and compared with saliva samples to which known quantities of TSP1 were added.

Saliva Collection

Unstimulated whole saliva was collected by expectoration into chilled centrifuge tubes and placed on ice. All donors, whether HIV seropositive or negative, had no active periodontal disease or oral lesions. Whole saliva was clarified by microcentrifugation (12,000×g for 10 minutes at 4° C.) and used immediately, while aliquots were stored at <20° C. Parotid saliva was collected from one gland using a modified Curby cup (Smith et al., "Immunological Features of Minor Salivary Gland Saliva," *J. Clin. Immunol.,* 7:449–454 (1987), which is hereby incorporated by reference). Submandibular salivary fluid was collected using surgical sponges (Weck-Cel) cut into approximately 0.25×0.5 cm rectangles and touched to blebs of fluid which formed at the duct orifi. Saliva was removed from sponges by centrifugation in polyethylene tubes, as described in Smith et al., "Immunological Features of Minor Salivary Gland Saliva," *J. Clin. Immunol.,* 7:449–454 (1987), which is hereby incorporated by reference. Protein content was estimated using a micro-BCA reagent kit (Pierce).

HIV-1 Infectivity Assays

CD4+T lymphoblastoid (SK23, Jurkat) and promonocytic (U937) cell lines, or peripheral blood mononuclear cells ("PBMC") obtained from HIV seronegative donors and activated with phytohemagglutinin ("PHA", 2 $\mu$g/ml for 72 hours), were cultured in RPMI 1640, 5% fetal bovine serum ("FBS", frozen/thawed and complement-inactivated 30 minutes at 56° C.), 100 U/ml penicillin and 100 $\mu$g/ml streptomycin (GIBCO/BRL, Grand Island, N.Y.). PBMC medium also contained 32 U/ml interleukin-2 (Sigma Chemical Co., St. Louis, Mo.). FBS samples were pre-screened to assure that levels of TSP were<10 $\mu$g/ml. Acute HIV infection was performed using HIV-1 isolate IIIB stock virus as previously described (Laurence et al., "Human Immunodeficiency Virus Infection of Helper T-Cell Clones: Early Proliferative Defects Despite Intact Antigen-Specific Recognition and Interleukin 4 Secretion," *J. Clin. Invest.,* 83:1843–1848 (1989); Laurence et al., "Human Immunodeficiency Virus Infection of Monocytes: Relationship to Fc-Gamma Receptors and Antibody-Dependent Viral Enhancement," *Immunology,* 70:338–343 (I 990), which are hereby incorporated by reference). Briefly, $2.5\times10^5$ target cells were exposed to stock virus at a moi of either 0.02 or 0.15 for 2 hours at 37° C., washed once with PBS, and re-plated in tissue culture-treated microwells with 0.3 ml fresh culture medium. At 3–4 days post-inoculation, one half of culture supernatant from each well was replaced with fresh medium. HIV activity was determined after 7 days using an ELISA antigen capture assay for HIV-1 p24 (gag) core protein (Dupont Medical Products, Boston, Mass.) of Triton X-100 solubilized culture supernatants.

Saliva and TSP1 Inhibition Assays

100 $\mu$l of HIV-1/IIIB inocula were mixed with 100 $\mu$l of various concentrations of whole saliva, salivary fluid fractions, or purified platelet TSP1 diluted in serum-free cell culture medium, and pre-incubated for 2 hours at 37° C. Then, 10-fold serial dilutions were added directly to target cell cultures for assay of infectivity. In some experiments, pre-incubated virus-saliva/TSP mixtures were filtered through 0.2 $\mu$m nitrocellulose syringe filters (Gelman Sciences, Ann Arbor, Mich.) prior to inoculation of target cells.

Salivary TSP1 Depletion Experiments

An affinity column for adsorption of TSP1 was prepared using fusion protein LFP75–155 coupled by N-hydroxysuccinimide to Sepharose (HiTRAP™, Pharmacia). Two ml of clarified whole saliva was diluted 1:1 in PBS and divided into two aliquots, one of which was applied to the TSP-binding GST/LIMPII column, the other to an identical column containing N-hydroxysuccinimide-linked GST alone. Columns were incubated 45 minutes at 37° C., then each flushed with 1 ml PBS. The final products represented 1:4 dilutions of saliva. TSP concentrations were determined before and after column adsorption by sandwich ELISA, and total protein assessed using the micro-BCA reagent kit.

Cell Surface Expression of CD4

CD4 surface expression on HIV-1 infected or uninfected U937 cells was evaluated by indirect immunofluorescence flow cytometry using anti-CD4 mAb Leu3, as detailed elsewhere (Laurence et al., "Human Immunodeficiency Virus Infection of Helper T-Cell Clones: Early Proliferative Defects Despite Intact Antigen-Specific Recognition and Interleukin 4 Secretion," *J. Clin. Invest.,* 83:1843–1848 (1989), which is hereby incorporated by reference).

Example 2

Characterization of a Putative TSP1 Binding Domain in HIV-1 env

Structural mapping studies have elucidated a TSP1 binding domain within the region encoded by CD36 exon 5 (Pearce et al., "Recombinant GST/CD36 Fusion Proteins Define a Thrombospondin Binding Domain: Evidence for a Single Calcium-Dependent Binding Site on CD36," *J. Biol. Chem.,* 270:2981–2986 (1995), which is hereby incorporated by reference). It has also been shown that the corresponding sequence of the CD36 homolog lysosomal integral membrane protein II ("LIMPII") (Vega et al., "Cloning, Sequencing, and Expression of a cDNA Encoding the Rat LIMP II, a Novel 74-kDa Lysosomal Membrane Protein Related to the Surface Adhesion Protein CD36," *J. Biol. Chem.,* 266:16818–16824 (1991); Calvo, D. et al., "The CD36, CLA-1 (CD36L1), and LIMP II (CD36L2) Gene Family: Cellular Distribution, Chromosomal Location, and Genetic Evolution," Genomics, 25:100–106 (1995), which are hereby incorporated by reference) bound TSP1 with high affinity, confirming a functionally identical domain (Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9) :4855–63 (1998), which is hereby incorporated by reference). Computer assisted motif analysis of 14 CD36 gene family homologs revealed highly conserved blocks implicating an evolutionarily maintained functional module designated CLESH-1 (Crombie et al., "Lysosomal Integral Membrane Protein LIMP II Binds Thrombospondin-I: Structure-Function Homology with the Cell Adhesion Molecule CD36 Defines a Conserved Recognition Motif," *J. Biol. Chem.,* 273(9):4855–63 (1998), which is hereby incorporated by reference). Using this sequence as the query in a pattern-based homology search to identify putative TSP binding sequences in proteins outside the CD36 gene family, CLESH-1 related sequences in HIV-1, HIV-2, and SIV-1 were identified. FIG. 1 shows the amino acid alignment of CD36/LIMPII CLESH-1 motifs with HIV-1 matched sequences. Strongest homology appeared as a split motif localized to domains C2 and C3 on either side of the V3 loop region of gp120. Homology was highest to LIMPII, with 62.5% identity, 87.5% similarity for the first half-site (C2 domain, 16 aa), and 55.6% identity, 88.9% similarity for the second half-site (C3 domain, 18 aa). Comparison with the clade B subtype consensus and two laboratory isolates used in this study (MN and LAI) shows that homology extends throughout both full-length motifs. The overall range of 30–36% identity, 79–84% similarity between LIMPII and HIV-1 isolates is comparable to 37% identity, 75% similarity observed between gene family members CD36 and LIMPII. This discovery prompted a biochemical approach to determine whether TSP1 could interact directly with gp120.

Figure 2A:
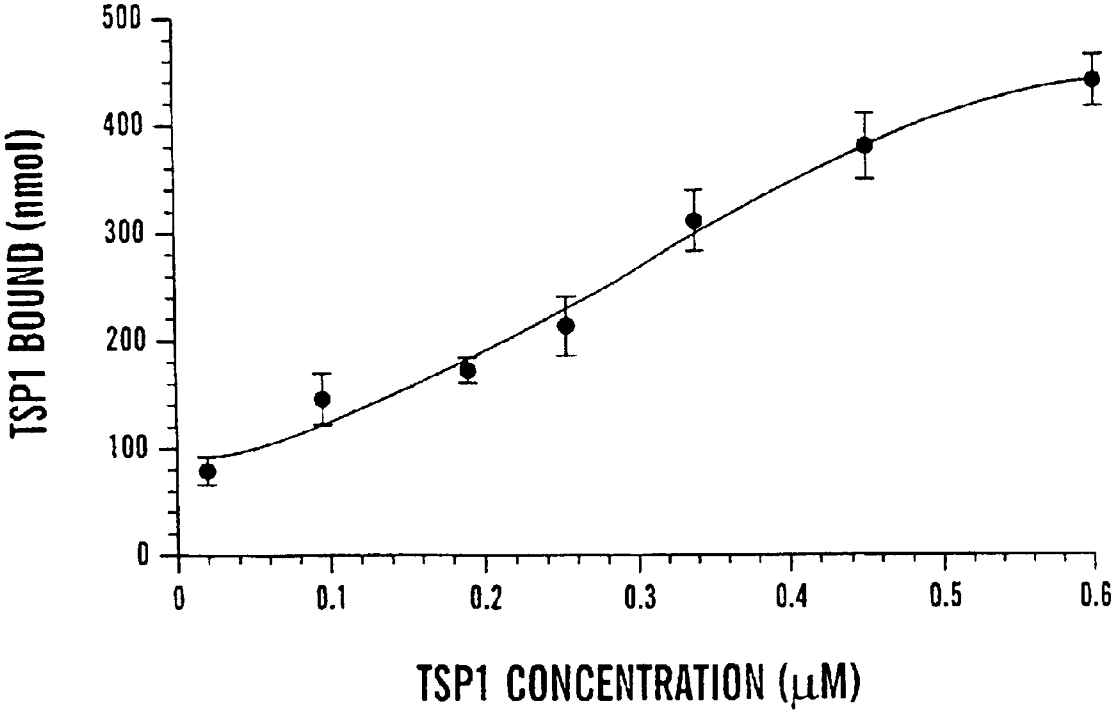
FIG. 2A is a graph showing concentration-dependent binding of 1251 TSP1 to LIMPII fusion protein. Increasing concentrations of soluble $^{125}$I-labeled TSP1 (1 nM–μM) were added to immobilized recombinant HIV-1 gp160 for 3 hours at 22° C., and bound TSP1 measured after extensive washing. Non-linear curve fit was generated with Excell™ version 5.0. Apparent affinity was estimated from Scatchard analysis. (n=2; error calculated as standard deviation, SD).
Figure 2B:
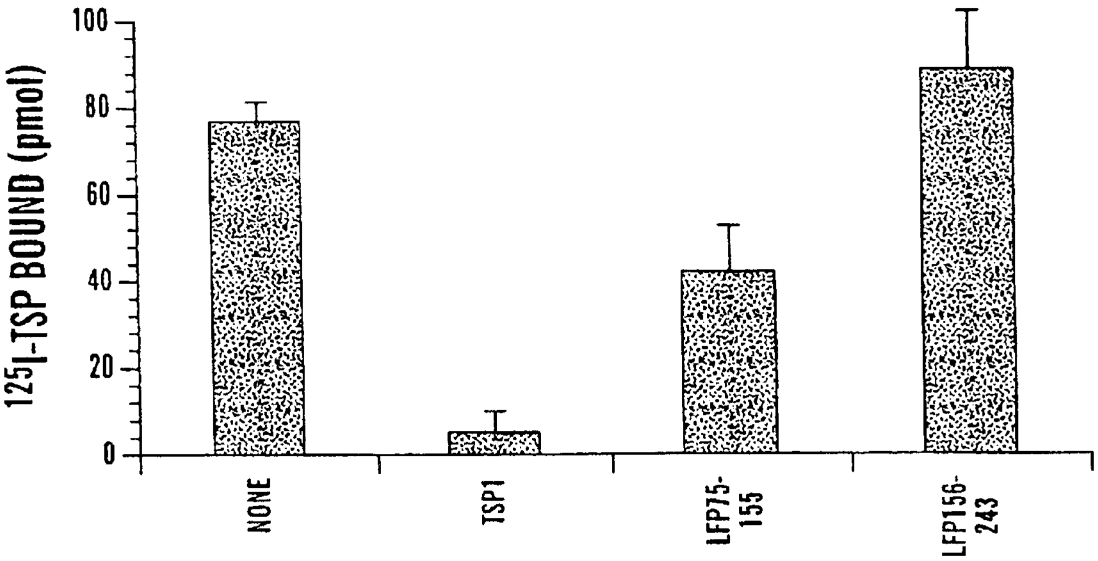
FIG. 2B is a graph showing competitive inhibition of $^{125}$-TSP1 for HIV-1 gp160, which demonstrates the specificity of the TSP1-HIV interaction. A fixed concentration of $^{125}$I-labeled TSP 1(50 nM) was added to immobilized rgp 160 in the absence or presence of 10-fold molar excess (0.5 μM) unlabeled TSP1, fusion protein LFP75–155 containing the LIMPII TSP binding domain (aa 75–155), or downstream fusion protein LFP 156–243. Samples were incubated, and bound TSP 1 was measured as in FIG. 2A. Plots represent single data sets of triplicate samples. (n=3, error as SD).

Solid phase binding assays were employed to assess direct binding of TSP1 to the HIV-1 envelope complex. FIG. 2A shows concentration-dependent, saturatable binding of radiolabeled soluble TSP1 to immobilized recombinant gp160 (gp120 non-covalently linked to transmembrane component gp41). An apparent affinity of approximately 250 nM was comparable to that demonstrated for binding of TSP1 to purified platelet CD36. Binding was effectively quenched in the presence of 10-fold molar excess unlabeled soluble TSP1 (FIG. 2B, 94±6% inhibition), demonstrating specificity. In addition, a LIMPII fusion protein LFP75–155 containing the TSP binding domain partially blocked binding (47±14% inhibition), while control fusion protein LFP156–243 representing downstream LIMPII sequences did not, supporting the existence of a functionally similar domain in HIV-1 env.

The CSVTCG (SEQ. ID. No. 1) peptides found in the Type 1 repeats of TSP1 are binding sites for CD36 and LIMPII (Crombie et al., "Lysosomal Integral Membrane Protein LIMP II Binds Thrombospondin-1: Structure-Function Homology with the Cell Adhesion Molecule CD36 Defines a Conserved Recognition Motif," *J. Biol. Chem.,* 273(9):4855–63 (1998); Asch et al., "Cellular Attachment to Thrombospondin: Cooperative Interactions Between Receptor Systems," *J. Biol. Chem.,* 266:1740–1745 (1991); Catimel et al., "Human Platelet Glycoprotein IIIb Binds to Thrombospondin Fragments Bearing the C-Terminal Region, and/or the Type I Repeats (CSVTCG Motif), but not to the N-Terminal Heparin-Binding Region," *Biochem. J.,* 284:231–236 (1992); Li et al., "Identification of SVTCG in Thrombospondin as the Conformation-Dependent, High Affinity Binding Site for its Receptor, CD36," *J. Biol. Chem.,* 268:16179–16184 (1993), which are hereby incorporated by reference).

Figure 3:
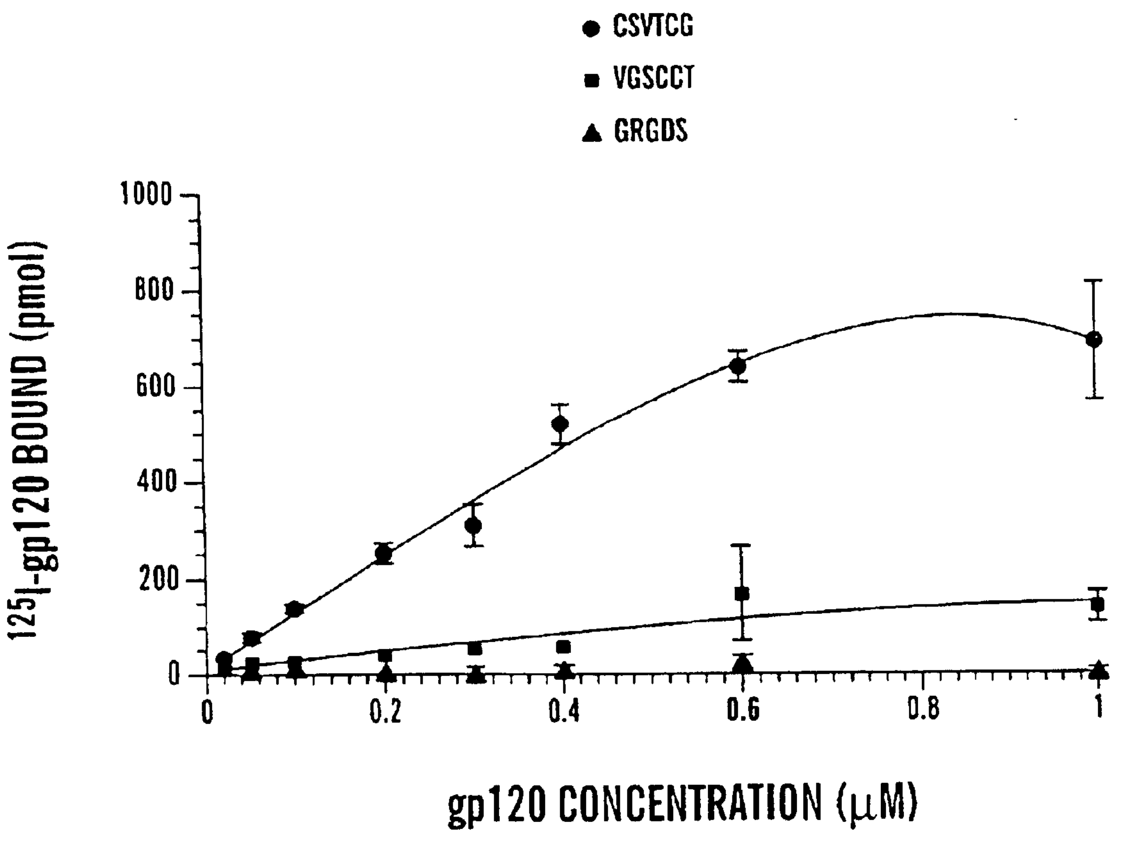
FIG. 3 is a graph showing how $^{125}$I-gp120 interacts with the CD36 binding peptide of TSP1. Increasing concentrations of soluble $^{125}$I-labeled recombinant gp120LAV (nM –1μM) were incubated with immobilized ligand for 2 hours at 37° C., and bound radioactivity measured as in FIGS. 2A and 2B. Shown are $^{125}$I-gp120 binding to CSVTCG (SEQ. ID. No. 1) peptide derived from TSP1 properdin-like Type 1 repeat, scrambled control peptide VGSCCT (SEQ. ID. No. 2), and GRGDS (SEQ. ID. No. 3) derived from TSP1 calcium binding Type 3 repeat. This plot represents a single data set of triplicate samples (72=2, errors as SD).

The gp120 envelope protein was tested to determine whether it shared this same specificity. Saturation isotherms showed significant binding of radiolabeled gp120 (LAI isolate) to immobilized CSVTCG peptide (SEQ. ID. No. 1), with an apparent affinity of 300 nM (FIG. 3). The activity was sequence-specific, as demonstrated by inefficient binding to scrambled control peptide VGSCCT (SEQ. ID. No. 2), or to an RGD-containing peptide similar to the GRGDA (SEQ. ID. No. 3) cell adhesion sequence of the last TSP1 Type 3 calcium-binding repeat. This is further evidence that the TSP1-gp120 interaction is mediated through a CD36/LIMPII-related structural domain.

Figure 4A:
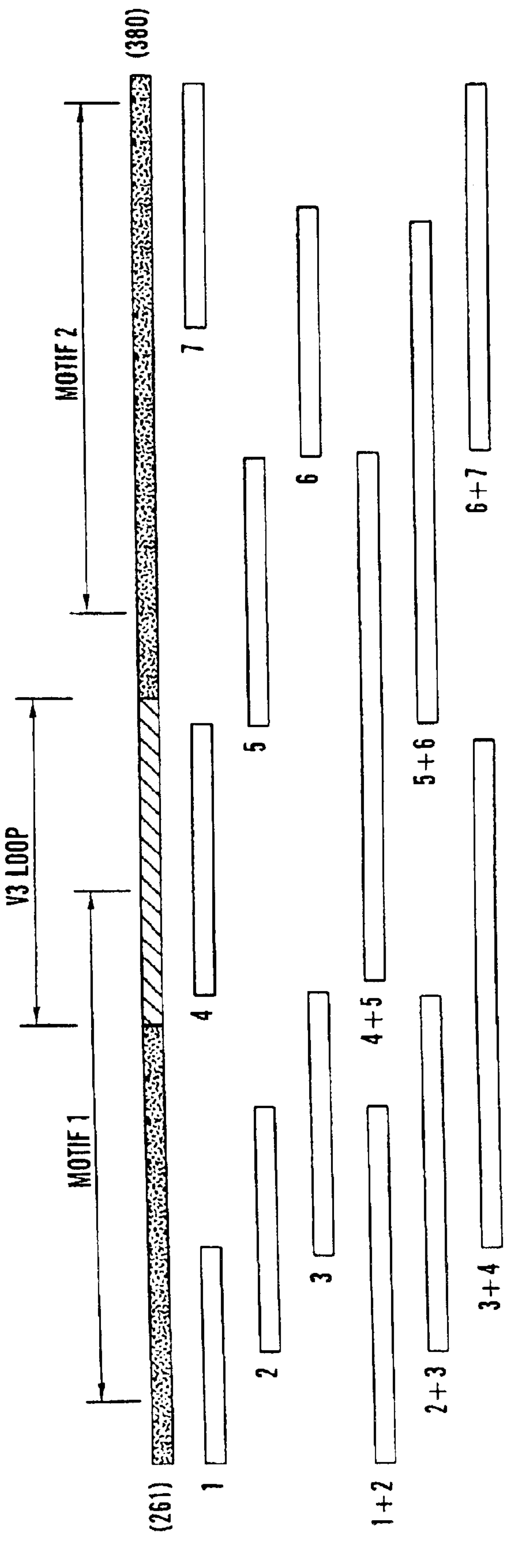
FIG. 4A is a map showing the position of synthetic gp120 peptides with respect to gp120 C2-V3-C3 domains and TSP binding motifs. A set of gp120MN peptides (~20 aa) were immobilized either singly (numbered 1–7) or in pairs as indicated. Corresponding amino acid positions are: I=aa 271–290; 2=aa 281–300; 3=aa 291–310; 4=aa 311–330; 5=aa 331–351; 6=aa 351–370; 7=aa 3361–380, 1+2 and 6+7 overlap by 10 aa; gp120=full length rgp120MN; V3 loop=aa 305–332; motif 1=aa 272–321; motif 2=aa 331–384.
Figure 4B:
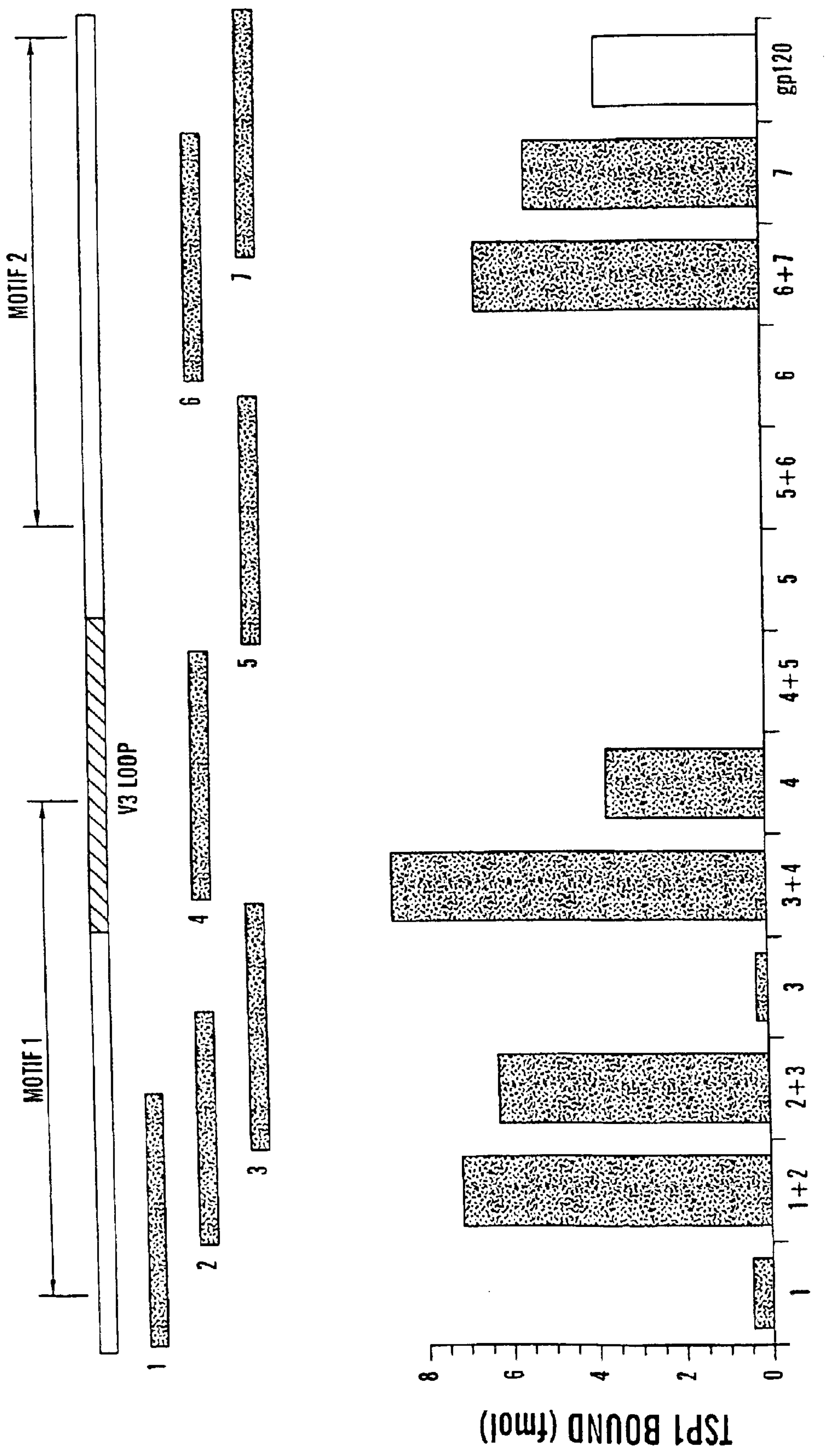
FIG. 4B is a graph showing the binding of $^{125}$I-TSP1 to gp120 peptides. Increasing concentrations of soluble $^{125}$I-labeled TSP 1 (25 nM–1μM) were added to immobilized gp120MN peptides. Samples were incubated, and bound TSP1 was measured as in FIG. 2. A single data set is shown for 25 nM TSP1 binding to 75–130 μmol peptide or 2 μmol gp120.

FIG. 4A shows the location of a series of 20 aa synthetic peptides with respect to gp120 domain structure (MN isolate). Given the constraints of the solid phase assay, peptides were immobilized either singly or in pairs, and tested for ability to bind radiolabeled TSP1. As shown in FIG. 4B, active peptides corresponded to regions of gp120 containing homologous CLESH-1 motifs. Peptide pairs that extended the represented motif sequence showed augmented binding as compared to either peptide alone. In addition, single peptides representing sequences outside strongly homologous split motif half-sites also showed significant TSP1 binding. Interestingly, a V3 containing peptide (#4, aa311–330) with TSP1 binding activity also displayed augmented binding in combination with an inactive C2 peptide within the first CLESH-1 motif (#3, aa291–310). These data suggest the presence of two component TSP1 binding elements in the predicted regions of gp120, including V3 sequences in the first motif, with the potential for interchangeable combinations of site usage, and possible TSP-mediated structural alterations that might disrupt conformation-dependent binding of gp120 to CD4 receptor.

Figure 5:
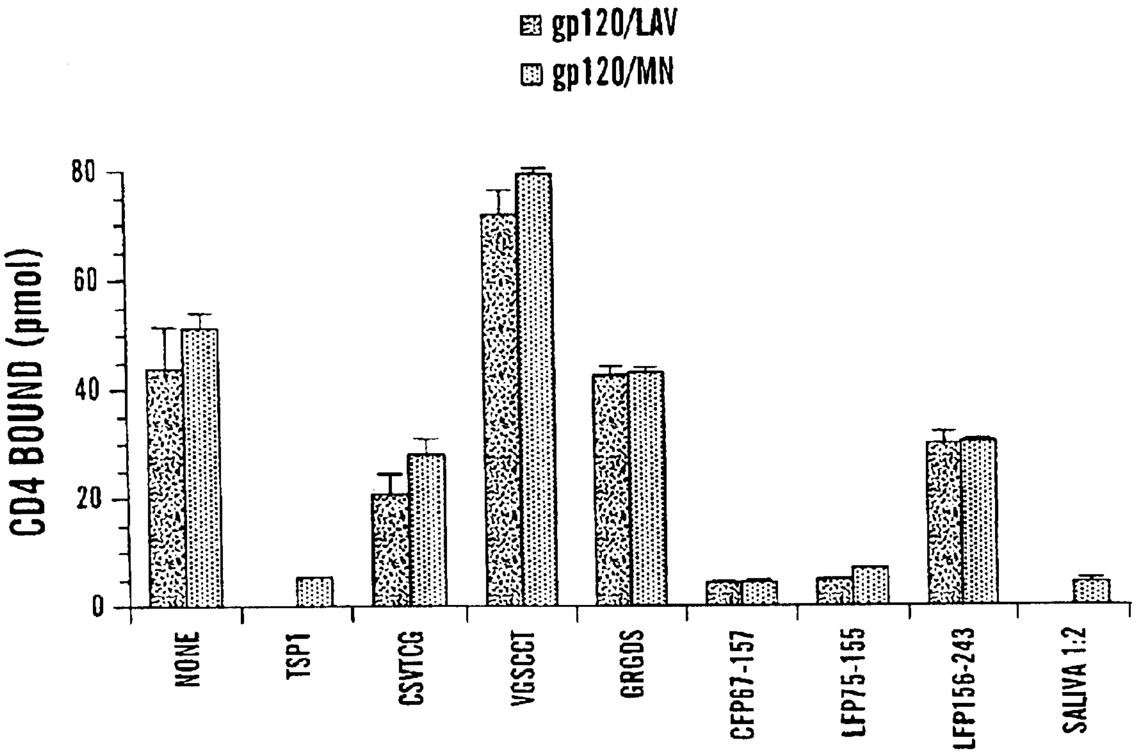
FIG. 5 is a graph showing competitive inhibition of $^{125}$I-CD4 binding to gp120. A fixed concentration of I$^{25}$1-labeled soluble recombinant CD4 (50 nM) was added to immobilized rgp 160 (solid MN or hatched LAV isolate-derived) in the absence or presence of 10-fold molar excess (0.5 μM) unlabeled TSP1, TSP1-derived peptides CSVTCG (SEQ. ID. No. 1) or GRGDS (SEQ. ID. No. 3), scrambled control peptide VGSCCT (SEQ. ID. No. 2), fusion proteins containing the TSP1 binding domain of CD36 (CFP, aa 67–157) or LIMPII (aa 75–155), downstream fusion protein LFP 156–243, or an equal volume of saliva (final 2-fold dilution). Samples were incubated, and bound TSP1 was measured as in FIG. 2. A single data set of triplicate samples (η=3, error as SD) is shown.

FIG. 5 shows competitive inhibition of radiolabeled CD4 binding to gp120 derived from two different viral isolates (MN and LAI). In the presence of a 10-fold molar excess of TSP1, complete inhibition of $^{125}$I-CD4 binding to immobilized gp120 was seen. The CSVTCG (SEQ. ID. No. 1) peptide showed partial but significant inhibition of CD4gp120 complex formation (53±9%), confirming a TSP-specific effect, while the RGD-containing peptide had little effect (4±4%), and the scrambled control actually enhanced binding. Consistent with structural homology data, TSP1-binding CD36- and LIMPII-derived fusion proteins proved strong competitors (both ~89% inhibition), whereas downstream LIMPII control protein had minimal effect (32±5%). For comparison, a 1:2 dilution of whole saliva was a potent inhibitor in this assay system. These observations support a role for salivary TSP1 as a direct inhibitor of HIV infectivity.

Example 3

Analysis of TSP1-Mediated Inhibition of HIV-1 Infectivity

As shown in Table 1 below, levels of TSP1 in whole saliva from either HIV+ or HIV− donors were at least 10-fold greater (1–12 μg/ml) compared to plasma.

Figure 6:
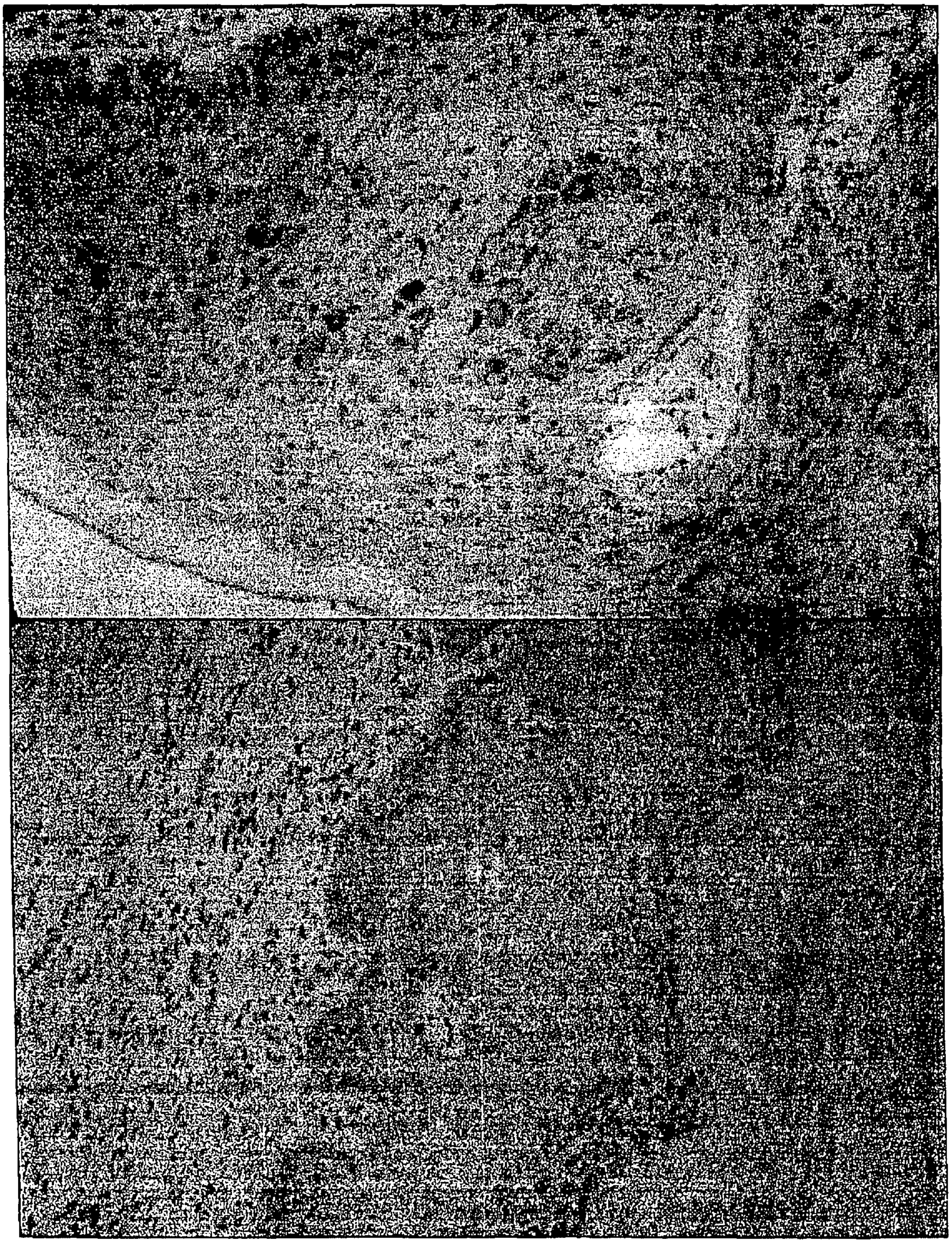
FIG. 6 is an image showing immunohistochemical detection of cell-associated TSP1 in human gingival mucosa. Fixed oral epithelial tissue thin section was incubated with polygonal antiserum reactive against both TSP 1 and TSP2 (lower panel), or with pre-immune serum (upper panel), followed by biotinylated second antibody, and developed using avidin-conjugated peroxidase. Brown deposits indicate sites of TSP reactivity (magnified 200×).

Amounts of TSP1 in parotid saliva fractions were equivalent to that of plasma, with the bulk of TSP 1 found in the submandibular secretions. These values are consistent with previous reports of anti-HIV activity predominately in submandibular and not parotid gland fluids (Fox et al., "Saliva Inhibits HIV-1 Infectivity," *J. Am. Dent. Assoc.,* 116:635–637 (1988); Archibald et al., "In Vitro Inhibition of HIV-1 Infectivity by Human Salivas," *AIDS Res. Hum. Retroviruses,* 6:1425–1432 (1990), which are hereby incorporated by reference). To document that elevated levels of TSP1 in saliva may be secondary to local production, rather than leakage and concentration from plasma, immunohistochemical staining of fixed tissue from oral mucosa was performed. Moderate to intense levels of TSP1-directed immuno-reactivity were evident on gingival epithelium (FIG. 6), confirming that cell-associated TSP1 may correspond to significantly high local concentrations in the oral cavity.

TABLE 1

Quantitation of TSP1 in Human Plasma and Saliva

| Sample Source | HIV Status | TSP1/TSP2 conc. (range) | n |
|---|---|---|---|
| plasma | negative | 0.25 (0.1–0.34) μg/ml | 8 |
| whole saliva | negative | 4.1 (1.1–12.8) μg/ml | 6 |
| | positive | 3.3 μg/ml | 2 |
| parotid | negative | 0.1 μg/ml | 1 |
| submandibular | negative | 2.5 μg/ml | 1 |

Figure 7:
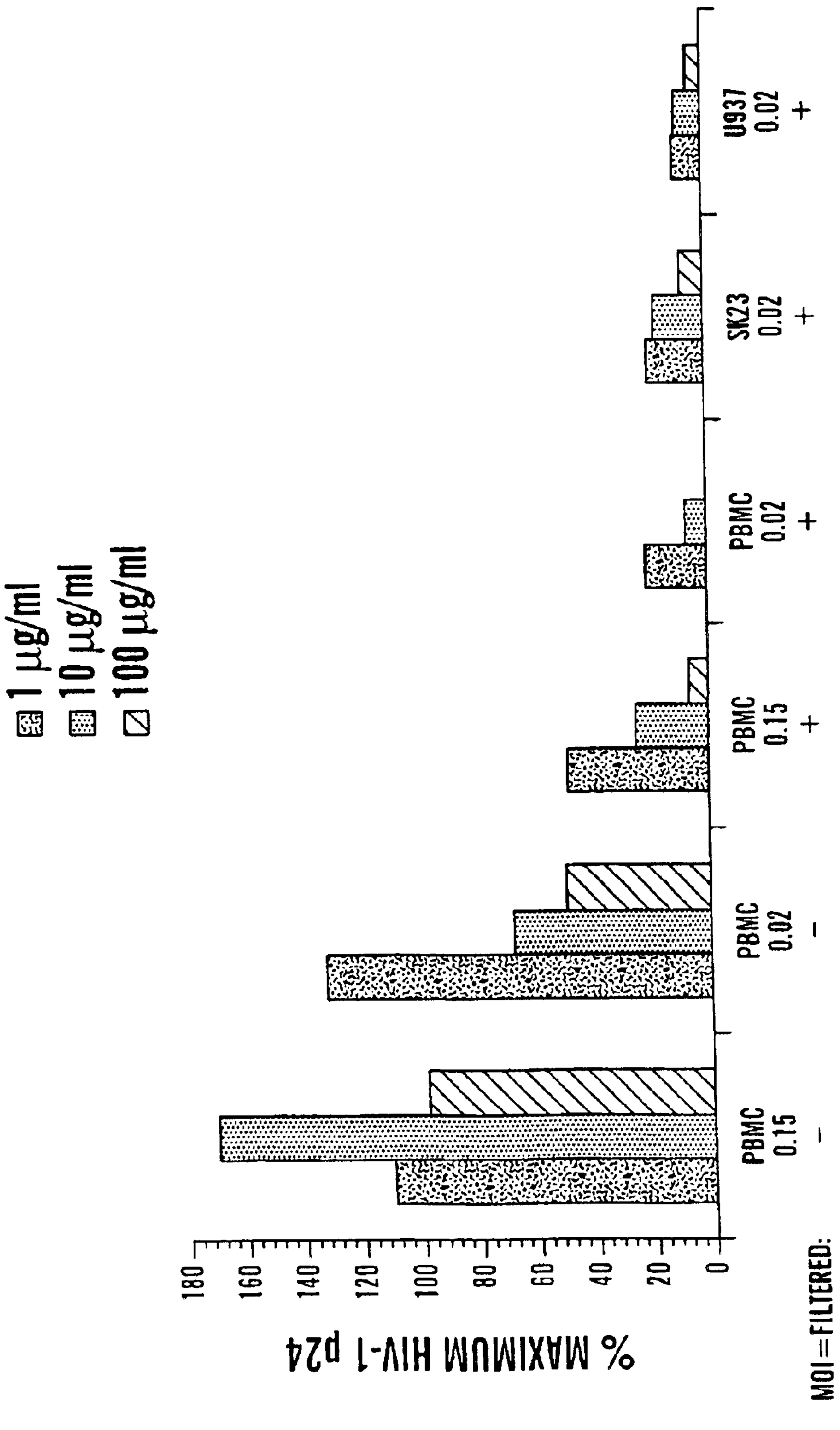
FIG. 7 is a graph showing the inhibitory effect of TSP 1 on HIV-1 infectivity. HIV-1 isolate IIIB was pre-incubated in the absence of TSP1, or with various concentrations of purified TSP1 for 1 hour at 37° C. Pre-incubated virus-TSP1 mixtures were added to target cells either directly (–), or first passed through 0.2 μm filters (+). Phorbol myrisate acetate ("PMA") activated primary peripheral blood mononuclear cells ("PBMC"), SK23 (T-cell line) or U937 (promonocytic line) were inoculated with the multiplicities of infection ("moi") indicated. After an additional 1 hour at 37° C., infected cells were washed, cultured for 7 days, and HIV-1 p24 antigen measured by ELISA. Inhibition is expressed for a single data set as percent of maximum p24 detected in the absence of TSP1.

To investigate whether purified TSP1 could inhibit HIV-1 infection similar to saliva, viral isolate IIIB was added to target cells after pre-incubation with TSP I. Many studies have shown that filtration of virus-saliva mixtures is required for maximum inhibition (Malamud et al., "Human Submandibular Saliva Aggregates HIV," AIDS Res. Hum. Retroviruses, 9:633–637 (1993); Fox et al., "Saliva Inhibits HIV-1 Infectivity," *J. Am. Dent. Assoc.,* 116:635–637 (1988); Fox et al., "Salivary Inhibition of HIV-1 Infectivity: Functional Properties and Distribution in Men, Women and Children," *J. Am. Dent. Assoc.,* 118:709–711 (1989); Bergey et al., "Interaction of HIV-1 and Human Salivary Mucins," *J. Acquired Immune Defic. Svndr.,* 7:995–1002 (1994), which are hereby incorporated by reference). The physiologic equivalent of such filtration is thought to be the constant cleansing of the oral cavity by salivary flow. Therefore, in some experiments, pre-incubated virus-TSP1 mixtures were passed through 0.2 μm filters. Different moi virus per target cell were tested in both systems. At concentrations found in saliva (2–10 μg/ml), TSP1 reduced HIV-1 infection of PHA-activated donor PBMC by >83% when pre-filtered, as measured by ELISA detection of p24 viral antigen (FIG. 7). This was comparable to a 1:2 dilution of whole saliva. In contrast, fibrinogen, another high molecular weight adhesive glycoprotein in saliva, had no effect in this system. Specificity was documented by abrogation of the inhibitory effect in the presence of a specific anti-TSP1 polyclonal antibody (107% of control p24), but not control IgG. Prolonged incubation of the TSP-virion mixture was unnecessary, as exposures as brief as 5 minutes appeared sufficient to reduce infectivity by >50% at 1 μg/ml TSP1. The TSP1 effect also was apparent for HIV-1 IIIB infection of CD4+ T-lymphoblastoid and monocytoid cell lines (SK23≧90.7% and U937≧83.0% inhibition, respectively). In addition, two monocytotropic strains of HIV-1, p13 and HA593 representing patient isolates obtained from the NIH AIDS Retroviral Repository, were susceptible to inhibition by purified TSP1. At viral moi's of 0.8, 100 μg/ml TSP1 inhibited HIV infectivity by ≧98±1%. In contrast to pre-filtration experiments, direct addition of TSP1 was able to inhibit HIV-1 by 50–75% only when a high concentration of TSP1 and a low moi inoculum was used (FIG. 7). In parallel assays, saliva could inhibit HIV-1 as a direct addition only when added in dilutions of less than 1:4. However, pre-incubation of virus with saliva permitted dilutions greater than 1:10. The results again are consistent with levels of TSP1 found in these dilutions of saliva.

To determine the extent of TSP1 contribution to saliva inhibition of HIV infectivity, clarified saliva samples were passed over affinity columns of immobilized TSP-binding LIMPII fusion protein LFP75–155 prior to virus pre-incubation. HIV-$1_{III\text{-}B}$ (0.15 moi) was admixed with clarified whole saliva that was untreated or first adsorbed with immobilized fusion proteins for 1 hour at 37° C. (final 1:4 dilute). Pre-incubated and filtered virus-saliva mixtures then were used to infect PHA-activated PBMC, and HIV-1 activity determined on day 7 post-inoculation as in FIG. 7. Percentages, shown in parentheses in Table 2 below, are relative to pre-adsorbed concentrations. Anti-HIV-1 inhibitory effect is expressed as percent decrease of maximum HIV-1 p24 antigen in the absence of saliva.

TABLE 2

Effect of TSP1 Depletion on Salivary Inhibition of HIV-1

| Saliva Adsorption | Protein conc. (pre-adsorbed conc.) | TSP1/TSP2 conc. | Percent Inhibition |
|---|---|---|---|
| None | 8.16 | 1.20 | 99.8 |
| TSP-affinity | 6.20 (76.0%) | 0.08 (6.3%) | 31.1 |
| GST Control | 7.52 (92.2%) | 1.18 (98.3%) | 99.7 |

Adsorption removed ~95% of TSP, as assessed by sandwich ELISA, while decreases in total protein was substantially less (~15%). TSP depletion correlated with >70% reduction in anti-viral activity, in contrast to saliva adsorbed using a control fusion protein affinity column (GST-1). The data suggest that TSP may account for a major proportion of HIV-specific inhibitory activity in saliva.

Figure 8:
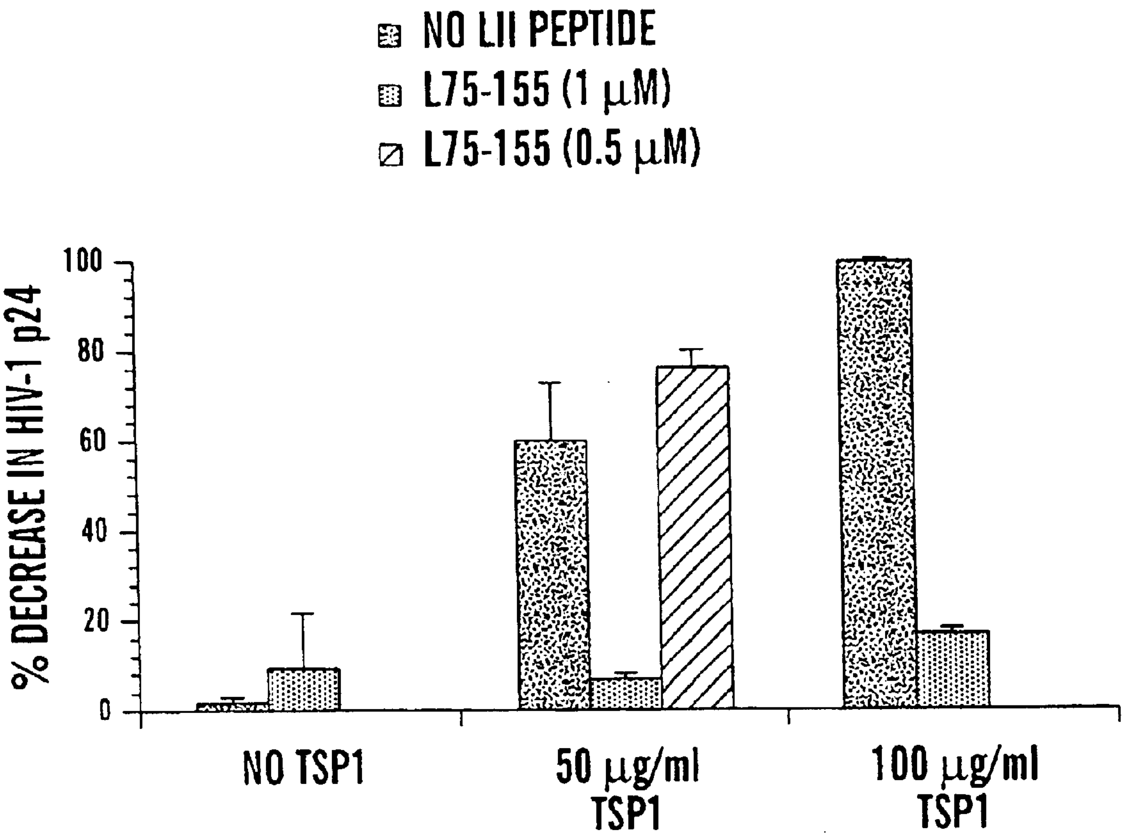
FIG. 8 is a graph showing competitive inhibition of TSP1 anti-HIV effect by LIMPII TSP1 binding domain. PMA-stimulated primary PBMC were infected with 0.02 moi HIV/IIIB that had been pre-incubated with TSP1 alone, or with LIMPII fusion protein LFP75–155 alone or in the presence of TSP1, and filtered prior to incubation as in FIG. 7. TSP-mediated inhibition is expressed as percent decrease in p24 relative to maximum p24 detected in the absence of TSP 1. Data shown represent the average of two independent experiments (error as SD).

To delineate further a TSP-specific effect, LIMPII TSP-binding peptide L75–155 (10 kDa product purified after removal of GST moiety by proteolytic cleavage) was included in HIV-TSP 1 pre-incubation mixtures as a competitor. FIG. 8 shows that 1 μM LIMPII peptide abrogated the inhibitory effect of even high concentrations of TSP1 (50–100μg/ml) by 83–90%. Incubation of virus in the presence of LIMPII peptide alone resulted in minimal decrease of HIV-1 infectivity (9%), suggesting that amounts of peptide able to block the TSP1 anti-viral effect were not sufficient to compete for HIV-1 env binding sites on PBMC target cells. The ability of the LIMPII peptide to restore infectivity supports a direct role for a CD36/LIMPII-related TSP1 binding domain on HIV-1 gp120, and provides further evidence of a common binding site on TSP1.

Another mechanism to explain TSP-mediated blockade to HIV infection would be a direct effect on target cells, whereby alterations in cell function would decreased the capacity to support productive infection. To address whether exogenous purified TSP1 induced down-modulation of the high affinity HIV receptor, CD4+ Jurkat and SK23 T-cell lines, as well as PHA-activated PBMC, were monitored for differences in CD4 surface expression after culture for 3 days in the absence or presence of 100 μg/ml TSP1. By flow cytometric analysis of cells stained with fluorescein-conjugated anti-CD4 IgG, no change in relative fluorescence intensity or percent CD4+cell was detected. Thus, TSP1 likely does not reduce cell susceptibility.

To examine whether HIV-I infection modulates TSP1 expression, TSP1 secretion was monitored in three groups of cells: an uninfected line of U937 promonocytic cells, U1.1 cells representing chronically infected U937 containing 2 stably integrated copies of HIV01/LAI, and U937 acutely infected with HIV-1 to high copy number (>1000 proviral copies/cell, (Laurence et al., "Human Immunodeficiency Virus Infection of Monocytes: Relationship to Fc-Gamma Receptors and Antibody-Dependent Viral Enhancement," Immunology, 70:338–343 (1990), which is hereby incorporated by reference). Cells were pre-incubated 1 hour in the presence or absence of phorbol myrisate acetate ("PMA"), a mitogenic inducer of HIV from chronically infected cells (Laurence et al., "Human Immunodeficiency Virus Infection of Monocytes: Relationship to Fc-Gamma Receptors and Antibody-Dependent Viral Enhancement," *Immunology,* 70:338–343 (1990), which is hereby incorporated by reference), also shown to stimulate TSP1 expression in cell lines (Varani et al., "Thrombospondin Production and Thrombospondin-Mediated Adhesion in U937 Cells," *Exp. Cell. Res.,* 195:177–182 (1991), which is hereby incorporated by reference). After 24 hours in culture medium (RPMI 1640 with 5% FCS), cells were switched to serum-free medium for an additional 18 hours, then supernatants were collected for TSP1 quantitation by ELISA. As shown in Table 3 below, HIV-1 infection did not diminish TSP1 production, although acute infection blunted the response to PMA induction of TSP1.

TABLE 3

Production of TSP by Monocytoid Cells in Presence/Absence of HIV-1 Infection

| Cell Line | Infection Status | PMA (5 ng/ml) | TSP1/TSP2 conc. (ng/ml) |
|---|---|---|---|
| U937 | parental, uninfected | − | <5 |
| U937 | promonocytic line | + | 51 |
| U1.1 | U937, chronic | − | 50 |
| U1.1 | 2 stable copies LAI | + | 125 |
| U937/HIV | acute, high copy | − | 180 |
| U937/HIV | IIIB (0.02 moi) | + | 135 |

The present invention concerns, in part, the identification of a TSP1 binding site in the C2 and C3 regions of gp120, conserved areas of the HIV envelope which are important in binding to CD4, and the demonstration of direct interaction between gp120 and a specific cell adhesion sequence found in the TSP1 type I repeat. Characterization by in vitro binding and competition studies substantiates that these CD36/LIMPII-related CLESH-1 motifs in gp120 represent authentic TSP1 binding domains. The physiological significance of TSP1-gp120 complex formation is supported by observations that: salivary inhibition of HIV-1 infectivity was markedly reduced by affinity depletion of TSP1; saliva samples that block infection following filtration contained levels of TSP1 that correlate with inhibitory concentrations of purified TSP1; and higher amounts of TSP1 required to block HIV-1 infectivity in vitro are comparable to the greater quantities of saliva required to obtain an anti-viral effect (Archibald et al., "In Vitro Inhibition of HIV-1 Infectivity by Human Salivas," *AIDS Res. Hum. Retroviruses,* 6:1425–1432 (1990); Bergey et al., "Interaction of HIV-1 and Human Salivary Mucins," *J. Acquired Immune Defic. Syndr.,* 7:995–1002 (1994), which are hereby incorporated by reference). Our findings establish a distinct mechanism to explain HIV-specific blockade of transmission via saliva.

The likelihood that HIV inhibitors in saliva identified in vitro are active in vivo is bolstered by two lines of evidence. First, in a study of 48 HIV+ patients, 88% of PBMC samples, but no saliva samples, were positive for replication-competent HIV (Qureshi et al., "Prevalence of HIV-1 Proviral DNA an Virion-Associated RNA in Saliva," *J. Dent. Res.,* 73:2564A (1994), which is hereby incorporated by reference). Second, recovery rates for HIV in saliva do not differ before and after dental procedures accompanied by bleeding into the oral cavity (Moore et al., "HIV Recovery from Saliva Before an After Dental Treatment: Inhibitors May Have a Crucial Role in Viral Inactivation," *J. Am. Dent. Assoc.,* 124:67–74 (1993), which is hereby incorporated by reference), indicating that free virus from blood was removed or inactivated. The fact that HIV is not found within salivary ancinar and ductal elements (Fox, "Saliva and Salivary Gland Alterations in HIV Infection," *J. Am. Dent. Assoc.,* 122:46–48 (1991), which is hereby incorporated by reference) implies that while virions and infected cells may traffic into the salivary glands, they cannot establish a productive infection.

TSP1 is synthesized in low amounts by monocytes/macrophages, epithelial cells, fibroblasts, smooth muscle cells, pneumocytes, and endothelial cells, and in larger quantities by platelets (Lahav, editor, "Thrombospondin," *CRC Press,* (1993), which is hereby incorporated by reference). However, HIV may be exposed to levels of TSP1 over 2-log higher on surfaces in the oral cavity. The fluid distribution of TSP1, with very low concentrations in plasma, sweat, tears, and urine, reflects the relative frequency with which HIV can be isolated from these secretions, but not from saliva. Breast secretions present another issue. HIV can be cultured from some samples of breast milk, which has been implicated in HIV transmission. Colostrum often contains high concentrations of TSP1 (upwards of 145 μg/ml), while lower, more variable amounts (to <1 μg/ml) have been measured in other breast secretions (Dawes et al., "Thrombospondin in Milk, Other Breast Secretions and Breast Tissue," *Sem. Thromb. Heost.,* 13:378–384 (1987), which is hereby incorporated by reference). However, HIV has not been recovered from breast milk devoid of cells (Guay et al., "Detection of Human Immunodeficiency Virus Type 1 (HIV-1) DNA and p24 Antigen in Breast Milk of HIV-1-Infected Ugandan Women and Verticle Transmission," *Pediatrics,* 98:438444 (1996), which is hereby incorporated by reference), and breast milk contains factors which inhibit HIV infection (VandePerre et al., "Infective and Anti-Infective Properties of Breast Milk from HIV-1 Infected Women," Lancet, 341:914–918 (1993), which is hereby incorporated by reference), one of which may be TSP.

The concept that an extracellular matrix molecule may serve as an inhibitor of microbial pathogens is not new. For example, fibronectin ("FN") binds free gp120 (Su et al., "Interaction of the Envelope Glycoprotein of Human Immunodeficiency Virus with Clq and Fibronectin Under Conditions Present in Saliva," *Mol. Immunol.,* 28:811–817 (1991), which is hereby incorporated by reference), and thereby might sequester HIV virions. The compartmentalization of FN in gingival crevicular fluid, whole and submandibular saliva, but not parotid fluid (Tynelius-Bratthall et al., "Fibronectin in Saliva and Gingival Crevices," *J. Period. Res.,* 21:563–568 (1986), which is hereby incorporated by reference), parallels our findings with TSP. However, concentrations required to inhibit HIV infectivity in vitro exceed those found in saliva by 10-fold. While high levels of FN are present in plasma (–300 μg/ml) (Torre et al., "Plasma Fibronectin Concentrations in Patients with Human Immunodeficiency Virus Infection," *J. Clin. Pathol.,* 43:560–562 (1990), which is hereby incorporated by reference), so is recoverable infectious HIV. In fact, FN actually may facilitate HIV-mediated syncycium formation (Ushijima et al., "Effect of Serum Components on Syncytium Formation and Virus Production by Cells Infected with Human Immunodeficiency Viruses In Vitro," *AIDS Res. Hum. Retroviruses,* 8:513–520 (1992), which is hereby incorporated by reference), and promote the growth of AIDS-KS (Kaposi sarcoma) cells constitutively expressing high levels of FN receptor (Barillari et al., "The RGD Motif and the Integrin Receptors are Involved in the Vascular Cell Growth and Adhesive Properties of Extracellular HIV-1 Tat Protein," *J. AIDS,* 6:688A (1993), which is hereby incorporated by reference), bringing further into question the physiological significance of FN-gp120 binding. In contrast, TSP1 proteolytic fragments and peptides show opposite effects, inhibiting KS/endothelial cell proliferation (Taraboletti et al., "Platelet Thrombospondin Modulates Endothelial Cell Adhesion, Motility, and Growth: A Potential Angiogenesis Regulatory Factor," *J. Cell Biol.,* 111:765–772 (1990); Roberts et al., "Modulation of Tumor Growth In Vitro and In Vivo by Stable Analogs of Thrombospondin Peptides," *AIDS Res. Hum. Retroviruses,* 21:S73 (1995), which are hereby incorporated by reference).

Defining the relationship between salivary inhibitors of HIV for in vivo versus in vitro model systems is important. Concentrations of TSP1 required to inhibit HIV infectivity by <50% following direct addition were equivalent to that found in dilutions of saliva used in HIV inhibition experiments by other investigators (Malamud et al., "Human Submandibular Saliva Aggregates HIV," *AIDS Res. Hum. Retroviruses,* 9:633–637 (1993); Fox et al., "Saliva Inhibits HIV-1 Infectivity," *J. Am. Dent. Assoc.,* 116:635–637 (1988); Fox et al., "Salivary Inhibition of HIV-1 Infectivity: Functional Properties and Distribution in Men, Women and Children," *J. Am. Dent. Assoc.,* 118:709–711 (1989); Bergey et al., "Interaction of HIV-1 and Human Salivary Mucins," *J. Acquired Immune Defic. Svndr.,* 7:995–1002 (1994), which are hereby incorporated by reference). Much lower doses of TSP1 were required to abrogate HIV infectivity when HIV-TSP mixtures were pre-filtered, suggesting aggregation of virion-TSP1 complexes as a potential mechanism of inhibition. The requirement for pre-filtration may have its in vivo counterpart in the continued cleansing of oral surfaces by salivary flow, with elimination of enmeshed viral particles from potential attachment sites. Experiments testing direct inhibition by whole saliva are complicated by the fact that additional salivary components may contribute to the anti-HIV effect. Indeed, TSP1 affinity depletion removed only 70% of the HIV-inhibitory activity. In addition, nonspecific antiviral phenomena may occur with saliva dilutions of 1:1 to 1:4 (Liuzzi et al., "Analysis of HIV-I Load in Blood, Semen and Saliva: Evidence for Different Viral Compartments in a Cross-Sectional and Longitudinal Study," *AIDS,* 10:F10–F56 (1996), which is hereby incorporated by reference). For example, highly charged sulfated polysaccharides, such as dextran sulfate and salivary mucins, present nonspecific anionic charge barriers to CD4-gp120 interactions at high concentrations (Amory et al., "The Large Molecular Weight Glycoprotein MGI, a Component of Human Saliva, Inhibits HIV-1 Infectivity," *Clin. Res.,* 40:51A (1992); Baba et al., "Novel Sulfated Polysaccharides: Dissociation of Anti-Human Immunodeficiency Virus Activity from Anti-Thrombin Activity," *J. Infect. Dis.,* 161:208–213 (1990), which are hereby incorporated by reference).

The presence of properdin-related sequences and properdin binding activity described for gp120 and gp41 (Stoiber et al., "Human Complement Proteins C3b, C4b, Factor H and Properdin React with Specific Sites in gp120 and gp41, the Envelope Proteins of HIV-1," *Immunobiol.,* 193/1:98–113 (1995), which is hereby incorporated by reference) support the functional significance of our sequence search results. The CSVTCG (SEQ. ID. No. 1) motif is found in two of the three Type 1 properdin/malaria-like repeats of TSP I. Consistent with homologies detected between CD36/LIMPII TSP1 binding domains and conserved sequences surrounding the V3 region of gp120, in vitro binding and peptide inhibition data indicate a highly specific gp120 interaction mediated through this CLESH-1 site. A high affinity TSP1 binding site on gp120 traversing the cysteine bridge of the V3 loop was suspected. However, envelope peptide mapping data suggested the presence of two full-length functional sites, with potential for direct involvement of the V3 loop, and presented a more complex model in which multiple or sequential site utilization is possible. Discontinuity created by intervening residues between the first and second motif half-site could induce conformational strain to distort or physically disrupt V3 loop integrity, with profound negative effects on gp120-CD4 association. Binding of TSP to the first highly homologous half-site in the C2 domain might lead to subsequent binding to weakly homologous downstream residues extending into the V3 loop, freeing the second full-length TSP binding site in the C3 domain. The second motif -encompasses a serine pair, KQSS (SEQ. ID. No. 4), shown to be critical for CD4 binding (Kowalski et al., "Functional Regions of the Envelope Glycoprotein of Human Immunodeficiency Virus Type 1," *Science,* 237:1351–1355 (1987), which is hereby incorporated by reference). Mechanistically, TSP1 could compete directly with CD4, occupying an identical or overlapping site. Alternatively, the bulky TSP1 trimer may sterically block access to the CD4 binding site, as well as V3 loop determinants. This model could explain why only partial inhibition is seen using CSVTCG peptides (SEQ. ID. No. 1). Elucidation of the molecular basis for TSP1 interference of CD4-gp120 association awaits additional structural studies.

Anti-HIV activities vary quantitatively among individual saliva donors. There also are differences in whether filtration is required to detect an inhibitory effect (Nagashunmugam et al., "Human Submandibular Saliva Specifically Inhibits HIV Type 1," *AIDS Res. Hum. Retroviruses,* 13:371–376 (1997), which is hereby incorporated by reference). In general, however, titers of salivary inhibitory factors decline with disease progression, in parallel with decreased total protein concentrations (Lal et al., "Pilot Study Comparing the Salivary Cationic Protein Concentrations in Healthy Adults and AIDS Patients: Correlation with Antifungal Activity," *J. AIDS,* 5:904–914 (1992), which is hereby incorporated by reference). There is a greater chance of HIV recovery from saliva with advancing clinical stage, albeit the rate is still low in comparison with other body fluids (Moore et al., "HIV Recovery from Saliva Before an After Dental Treatment: Inhibitors May Have a Crucial Role in Viral Inactivation," *J. Am. Dent. Assoc.,* 124:67–74 (1993), which is hereby incorporated by reference). This raises the possibility that HIV may directly suppress production of saliva inhibitory factors, or elicit blocking molecules. TSP1 production is down-regulated by DNA viruses (Mosher, "Physiology of Thrombospondin," *Ann. Rev. Med.,* 41:85–97 (1990), which is hereby incorporated by reference), and production of FN is depressed by retroviral infection (Adams et al., "Modulation of Fibronectin Gene Expression in Chondrocytes by Viral Transformation and Substrate Attachment," *J. Cell. Biol.,* 105:483–488 (1987), which is hereby incorporated by reference). However, production of TSP1 by PMA-activated monocytes was not affected by HIV infection in our system, and acute or chronic HIV infection actually upregulated TSP1 production by these cells, although to levels lower than shown to affect HIV infectivity (<2ng/ml). Regardless of normal levels of TSP1 production in the oral cavity, mechanical alterations also may contribute to decreased saliva inhibitory activity in vivo, as decreased salivary flow rates and buffering capacity correlate with advanced HIV infection (Madigan et al., "Caries and Criogenic Flora in HIV-Positive Children Versus Uninfected Children," *J. Dent. Res.,* 73:1898A (1994), which is hereby incorporated by reference).

The location of TSP1 binding motifs in highly conserved HIV domains makes these sites attractive targets for blocking agents that would be broadly reactive to HIV-1 and HIV-2 substrains. The ability of TSP 1 to block CD4-gp120 complex formation suggests the potential utility of this matrix molecule in the development of non-toxic natural inhibitors of local transmission of HIV-1, perhaps as a candidate topical adjuvant that could serve as a preventive physical barrier for rectogenital and GI tract mucosa.

Example 4

RANTES Binding to TSP1

Further analysis of the CLESH-1 structure was performed by searching a crystal structure database that combines primary sequence homology and predicted secondary structure. The CLESH-1 sequence of LIMPII was used to perform this search using BEAUTY as described above. The highest scoring match for LIMPII was to RANTES, a β-chemokine that competes with gp120 for binding to the CCR5 co-receptor for M-tropic HIV-1 strains.

Figure 9:
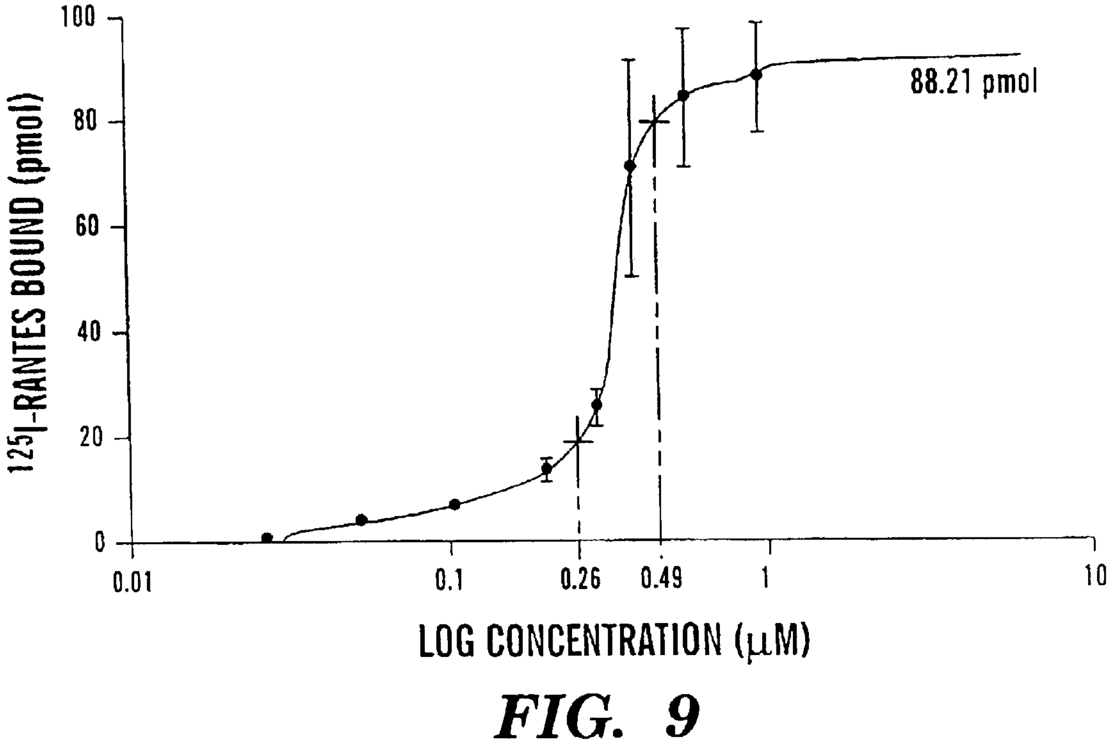
FIG. 9 is a graph showing the binding of $^{125}$I-RANTES to TSP1. Increasing concentrations of soluble $^{125}$I-labeled RANTES (0.01 μM –10.0 μM) were added to immobilized TSP1. Samples were incubated and bound $^{125}$I-labeled RANTES measured by solid-binding radio-amino assay.
Figure 10:
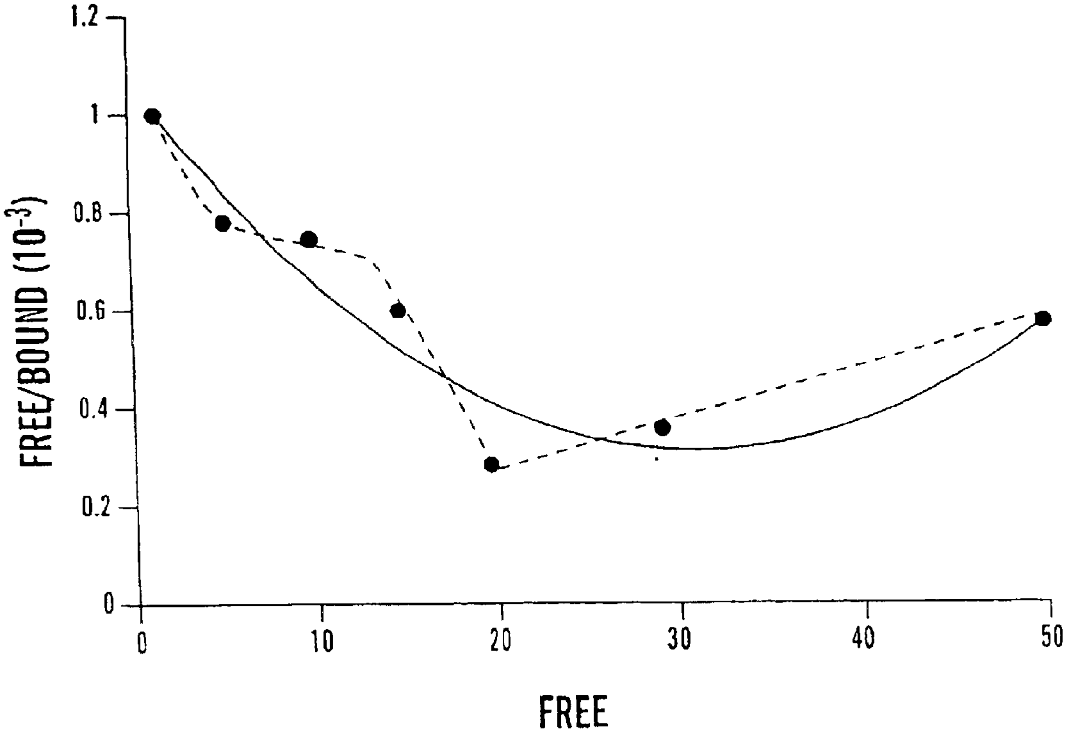
FIG. 10 is a graph showing the Hanes analysis of "$^{125}$-RANTES binding to immobilized TSP1. The Hanes analysis provides a measure of assessing the possibility of binding one or more factors to a given molecule.

In solid phase assays, $^{125}$I-RANTES binded to immobilized TSP. Saturatable binding showed biphasic higher order kinetics, half maximal at ~330 nM (FIG. 9). Estimated stoichiometry at equilibrium was low (~0.5 RANTES molecule for every 10 TSP monomer), although the steep slope of the second phase indicated a cooperative interaction (Hanes plot, FIG. 10). One interpretation of the data is that RANTES homodimerization is favored over binding to TSP. At a concentration that shifts equilibrium toward formation of the heterologous complex, positive cooperativity likely reflects a higher apparent affinity of RANTES monomers for binding to TSP, with an increase in monomers being a function of the odd number of sites presented by TSP homotrimers. The ability of RANTES to bind directly to TSP suggests that RANTES may compete for TSP binding sites in gp120, and supports further the potential for CLESH-1-containing conserved domains of gp120 to share structural homology with the β-turn configuration of RANTES.

Example 5

CD4 Binding to TSP1 and the CSVTCG TSP Analog

Figure 12:
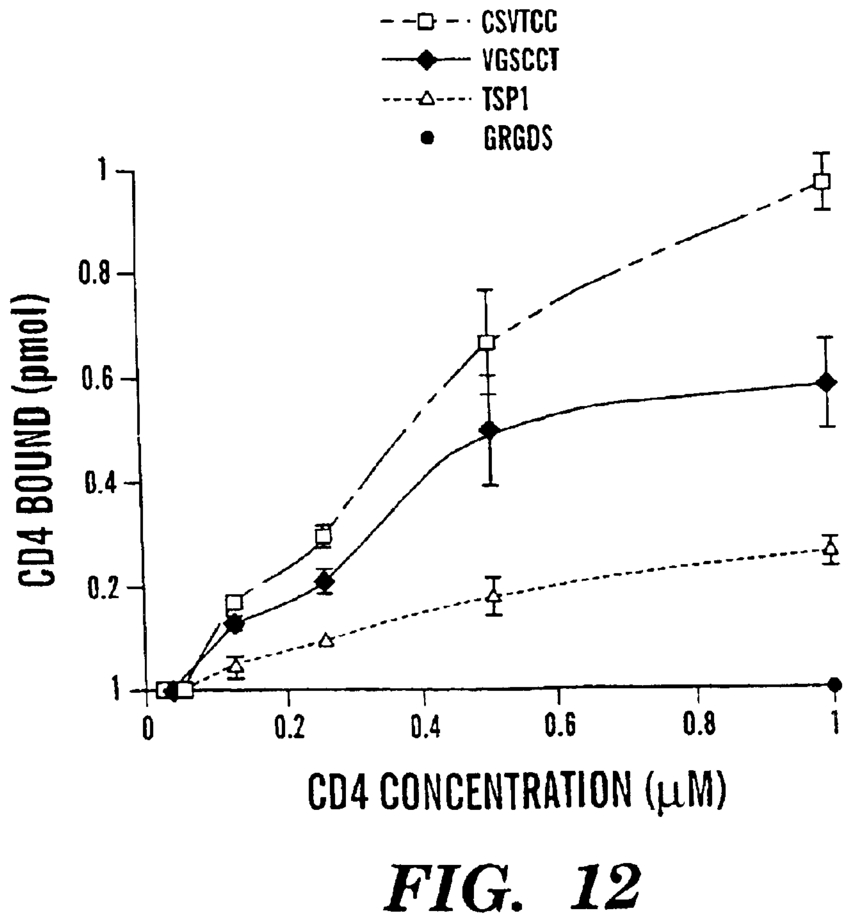
FIG. 12 is a graph showing the binding of $^{125}$I-CD4 to TSP1 and a TSP analog. Increasing concentrations of soluble $^{125}$I-labeled CD4 (0.1μM –1.0 μM) were added to immobilized TSP1, CVSTCG polypeptide (SEQ. ID. No. 1). Samples were incubated and bound $^{125}$I-labeled CD4 measured by solid-binding radio-amino assay, VGSCCT peptide (SEQ. ID. NO. 2), or GRGDS peptide (SEQ. ID. NO. 3).

In solid phase assays, $^{125}$I-CD4 binded to immobilized TSP1 in a concentration dependent saturatable manner, with biphasic kinetics. The results of this study are shown in FIG. 12. Additionally, $^{125}$I-CD4 binded directly to the TSP analog having an amino acid sequence CSVTCG (SEQ. ID. No. 1), implicating the presence of a CD36-related binding site (i.e., a CLESH-1 motif) in CD4. These results are consistent with TSP saturating CLESH-1 sites in gp120, which is believed to free properdin sequences in gp120 to form a tri-molecular complex with CD4.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for suppressing infectivity of HIV-1 across a mucosal surface comprising:

contacting the HIV-1 or a cell targeted by HIV-1 with an effective amount of either thrombospondin-1, thrombospondin-2, a fragment of thrombospondin-1 or thrombospondin-2 comprising the peptide of SEQ ID NO: 1, or a substance comprising the peptide of SEQ ID NO: 1, wherein said contacting suppresses infection by HIV-1 across the mucosal surface.

2. The method according to claim 1, wherein said method is carried out with an effective amount of thrombospondin-1 or thrombospondin-2.

3. The method according to claim 1, wherein said method is carried out with an effective amount of a substance comprising the peptide of SEQ ID NO: 1.

4. Ax The method according to claim 1, wherein said method is carried out by contacting the HIV-1 under conditions effective to bind the HIV-1 gp120 envelope protein.

5. The method according to claim 1, wherein said method is carried out by contacting the cell targeted by HIV-1 under conditions effective to bind to a CD4 receptor on the cell.

6. The method according to claim 1, wherein said contacting the HIV-1 or the cell is carried out intraorally, intrarectally, or intravaginally.

7. A method of inhibiting HIV-I infection in a patient comprising:

administering either thrombospondin-1, thrombospondin-2, a fragment of thrombospondin-1 or thrombospondin-2 comprising the =peptide of SEQ ID NO: 1 or a substance comprising the peptide of SEQ ID NO: 1 to a patient under conditions effective to inhibit HIV-I infection across a mucosal surface and binding to a CD4 receptor-positive cell.

8. The method according to claim 7, wherein said method is carried out by administering thrombospondin-1 or thrombospondin-2.

9. The method according to claim 7, wherein said method is carried out by administering a substance comprising the peptide of SEQ ID NO: 1.

10. The method according to claim 7, wherein said administering is intraorally, intravaginally, or intrarectally.

11. A method of blocking HIV-1 binding to a cell targeted by HIV-1 comprising:

contacting the HIV-1 or a CD4-positive cell targeted by HIV-1 with either thrombospondin-1, thrombospondin-2, a fragment of thrombospondin-I or thrombospondin-2 comprising the peptide of SEQ ID NO: 1, or a substance comprising the peptide of SEQ ID NO: 1 under conditions effective to block binding of the HIV-1 to the cell via the CD4 cell surface receptor.

12. The method according to claim 11, wherein said method is carried out with thrombospondin-1 or thrombospondin-2.

13. The method according to claim 11, wherein said method is carried out with a substance comprising the peptide of SEQ ID NO: 1.

14. The method according to claim 11, wherein said method is carried out by contacting the HIV-1 with a under conditions effective to bind the HIV-1 gp120 envelope protein and thereby block HIV-1 binding to the CD4 cell surface receptor.

15. The method according to claim 11, wherein said method is carried out by contacting the cell under conditions effective to bind to the CD4 cell surface receptor on the cell and thereby block HIV-1 binding to the CD4 cell surface receptor.

16. The method according to claim 3, wherein the substance comprising the peptide of SEQ ID NO: 1 is a fusion protein.

17. The method according to claim 9, wherein the substance comprising the peptide of SEQ ID NO: 1 is a fusion protein.

18. The method according to claim 13, wherein the substance comprising the peptide of SEQ ID NO: 1 is a fusion protein.

19. The method according to claim 2, wherein the thrombospondin-1 or thrombospondin-2 is substantially purified.

20. The method according to claim 2, wherein said method is carried out with thrombospondin-1.

21. The method according to claim 2, wherein said method is carried out with thrombospondin-2.

22. The method according to claim 8, wherein the thrombospondin-1 or thrombospondin-2 is substantially purified.

23. The method according to claim 8, wherein said method is carried out with thrombospondin-1.

24. The method according to claim 8, wherein said method is carried out with thrombospondin-2.

25. The method according to claim 11, wherein the thrombospondin-1 or thrombospondin-2 is substantially purified.

26. The method according to claim 11, wherein said method is carried out with thrombospondin-1.

27. The method according to claim 11, wherein said method is carried out with thrombospondin-2.

28. The method according to claim 1, wherein said method is carried out with a fragment of thrombospondin-1 or thrombospondin-2 comprising the peptide of SEQ ID NO: 1.

29. The method according to claim 28, wherein the fragment is a type I repeat of thrombospondin-1 or thrombospondin-2.

30. The method according to claim 28, wherein the fragment is the peptide of SEQ ID NO: 1.

31. The method according to claim 7, wherein said method is carried out with a fragment of thrombospondin-1 or thrombospondin-2 comprising the peptide of SEQ ID NO: 1.

32. The method according to claim 31, wherein the fragment is a type I repeat of thrombospondin-1 or thrombospondin-2.

33. The method according to claim 31, wherein the fragment is the peptide of SEQ ID NO: 1.

34. The method according to claim 11, wherein said method is carried out with a fragment of thrombospondin-1 or thrombospondin-2 comprising the peptide of SEQ ID NO: 1.

35. The method according to claim 34, wherein the fragment is a type I repeat of thrombospondin-1 or thrombospondin-2.

36. The method according to claim 34, wherein the fragment is the peptide of SEQ ID NO: 1.

* * * * *